(12) United States Patent
Liu et al.

(10) Patent No.: US 9,688,600 B2
(45) Date of Patent: Jun. 27, 2017

(54) PROCESSES FOR IMPROVING ACETIC ACID YIELD BY REMOVING IRON

(71) Applicant: CELANESE INTERNATIONAL CORPORATION, Irving, TX (US)

(72) Inventors: Yaw-Hwa Liu, Missouri City, TX (US); Mark O. Scates, Houston, TX (US)

(73) Assignee: CELANESE INTERNATIONAL CORPORATION, Irving, TX (US)

( * ) Notice: Subject to any disclaimer, the term of this patent is extended or adjusted under 35 U.S.C. 154(b) by 0 days.

(21) Appl. No.: 14/941,008

(22) Filed: Nov. 13, 2015

(65) Prior Publication Data

US 2016/0137578 A1    May 19, 2016

Related U.S. Application Data

(60) Provisional application No. 62/080,024, filed on Nov. 14, 2014.

(51) Int. Cl.

| C07C 51/12 | (2006.01) |
|---|---|
| C07C 51/47 | (2006.01) |
| C07C 51/44 | (2006.01) |
| B01J 31/40 | (2006.01) |
| C07C 51/487 | (2006.01) |

(52) U.S. Cl.
CPC ........... *C07C 51/12* (2013.01); *B01J 31/4046* (2013.01); *C07C 51/44* (2013.01); *C07C 51/47* (2013.01); *C07C 51/487* (2013.01)

(58) Field of Classification Search
CPC .......... C07C 51/44; C07C 51/47; C07C 51/12
See application file for complete search history.

(56) References Cited

U.S. PATENT DOCUMENTS

| 4,007,130 A | 2/1977 | Leach et al. |
|---|---|---|
| 4,894,477 A | 1/1990 | Scates et al. |
| 4,985,383 A | 1/1991 | Erpenbach et al. |
| 5,124,290 A | 6/1992 | Erpenbach et al. |
| 5,292,948 A | 3/1994 | Zoeller et al. |
| 5,416,237 A * | 5/1995 | Aubigne ............... C07C 51/12 562/406 |
| 5,466,876 A | 11/1995 | McClarron et al. |
| 5,625,095 A | 4/1997 | Miura et al. |
| 5,731,252 A | 3/1998 | Warner et al. |
| 6,066,762 A | 5/2000 | Yoneda et al. |
| 6,211,405 B1 | 4/2001 | Cheung et al. |
| 7,005,541 B2 | 2/2006 | Cheung et al. |
| 7,683,212 B2 | 3/2010 | Kojima et al. |
| 7,799,229 B2 | 9/2010 | Poole et al. |
| 8,242,040 B2 | 8/2012 | Poole et al. |
| 8,697,908 B2 | 4/2014 | Torrence et al. |
| 8,940,932 B2 | 1/2015 | Shimizu |
| 8,957,248 B2 | 2/2015 | Miura et al. |
| 9,006,483 B2 | 4/2015 | Shimizu et al. |
| 9,073,843 B2 | 7/2015 | Shimizu et al. |
| 9,115,071 B2 | 8/2015 | Shimizu et al. |
| 9,162,958 B2 | 10/2015 | Shimizu et al. |
| 2013/0264186 A1 | 10/2013 | Shimizu et al. |
| 2015/0368176 A1 | 12/2015 | Miura et al. |

FOREIGN PATENT DOCUMENTS

| EP | 0384652 A1 | 8/1990 |
|---|---|---|
| JP | 07025814 A * | 1/1995 |
| JP | H0867650 A | 3/1996 |
| JP | H10231267 A | 9/1998 |
| WO | 02/062740 A1 | 8/2002 |

OTHER PUBLICATIONS

International Search Report and Written Opinion of the corresponding International PCT application No. PCT/US2015/060536, dated Feb. 5, 2016, 12 pgs.
Third Party Observation received in the corresponding International Patent Application No. PCT/US2015/060536, submitted Mar. 13, 2017.
Title-"Control of propionic acid content in acetic acid production by carbonylation of methanol", Aug. 25, 2013, 20, pp. 50-52, p. 51, right column, line 4-13.
Title-"Control of formation of ethanol in methanol", Sep. 15, 2007, $5^{th}$ period, pp. 21-22, left column, lines 8-16.
Title-"A method to reduce ethanol content in purified methanol", Aug. 25, 2010, vol. 33, No. 4, pp. 225-227, p. 225, left column, line 2-9.
Title-"Purification of crude methanol", Jan. 15, 1997, 1997, $1^{st}$ period, pp. 1-5 and 11, p. 2, left column, line 24-right column, line 3.
Kirk-Othrner Encyclopedia of Chemical Technology $4^{th}$ Ed, Mass Transfer to Neuroregulators, a Wiley-Interscience publication; John Wiley & Sons, Inc., vol. 16, 1995, p. 554, lines 9-17.
IMPCA Methanol Reference Specifications, International Methanol Producers & Consumers Association, Dec. 9, 2010, p. 1.
Title: "Specification of ethanol content of methanol products", May 15, 2008, 2008, $3^{rd}$ period, pp. 52-54, p. 53, left column, lines 14-20.
Title: "Consideration for four-column distillation process for methanol production", Sep. 20, 1998, 1998, $9^{th}$ period, pp. 21-22.

* cited by examiner

*Primary Examiner* — Paul A Zucker
(74) *Attorney, Agent, or Firm* — Kilpatrick Townsend & Stockton LLP

(57) ABSTRACT

In a process for improving a carbonylation process, iron is removed to maintain an effective Space Time Yield (STY) of the rhodium catalyst of at least 80% of the maximum STY. The process comprises carbonylating methanol in a reactor in a reaction medium comprising water, a rhodium catalyst, methyl iodide and a halide salt, separating a portion of the reaction medium in a flash vessel to form a less volatile stream and a vapor product stream comprising acetic acid, recycling a liquid stream to the reactor, wherein the liquid stream comprises a portion of the less volatile stream and wherein the liquid stream comprises iron, and removing a portion of the iron from the liquid stream to maintain an effective STY of the rhodium catalyst of at least 80% of the maximum STY.

13 Claims, 7 Drawing Sheets

PROCESSES FOR IMPROVING ACETIC ACID YIELD BY REMOVING IRON

CROSS-REFERENCES TO RELATED APPLICATIONS

This patent application claims priority from U.S. Provisional Patent App. No. 62/080,024, entitled "Processes For Producing Acetic Acid," filed Nov. 14, 2014, the disclosure of which is incorporated herein by reference in its entirety.

FIELD OF THE INVENTION

This invention relates to processes for producing acetic acid and, in particular, to processes for improving the yield of acetic acid from a carbonylation reaction by removing iron from the carbonylation reaction medium.

BACKGROUND OF THE INVENTION

Among currently employed processes for synthesizing acetic acid, one of the most useful commercially is the catalyzed carbonylation of methanol with carbon monoxide as taught in U.S. Pat. No. 3,769,329, incorporated herein by reference in its entirety. The carbonylation catalyst contains rhodium, either dissolved or otherwise dispersed in a liquid reaction medium or supported on an inert solid, along with a halogen-containing catalyst promoter as exemplified by methyl iodide. The rhodium can be introduced into the reaction system in any of many forms. Likewise, because the nature of the halide promoter is not generally critical, a large number of suitable promoters, most of which are organic iodides, may be used. Most typically and usefully, the reaction is conducted by continuously bubbling carbon monoxide gas through a liquid reaction medium in which the catalyst is dissolved.

In the operation of the process for the carbonylation of methanol to acetic acid on a continuous basis, a solution containing the soluble catalyst complex is separated from the reactor effluent and recycled to the reactor. However, with operation over extended periods of time, corrosion products dissolve from the vessels of the metallurgy stream, e.g., iron, nickel, molybdenum, chromium, and the like, and build up in the catalyst recycle stream. Such corrosion metals, if present in sufficient quantities, are known to interfere with the carbonylation reaction or accelerate competing reactions such as the water-gas shift reaction (carbon dioxide and hydrogen formation) and methane formation. Thus, the presence of these corrosion metal contaminants has an adverse effect on the process, in particular, a consequent loss in carbon monoxide productivity. Further, corrosion metals can react with ionic iodine thus making this component of the catalytic system unavailable for reaction with rhodium and causing instability in the catalyst system. In view of the high cost of the rhodium-containing catalyst, replacement of spent catalyst can be effected only at a prohibitive cost.

U.S. Pat. No. 8,242,040, herein incorporated by reference, teaches a process for the removal of corrosion metal contaminants from a carbonylation catalyst solution comprising an iridium and/or rhodium carbonylation catalyst, an alkali and/or alkaline earth metal and corrosion metal contaminants. The catalyst solution is contacted with a cation exchange resin having its active sites partially loaded with a sufficient amount of alkali and/or alkaline earth metal to maintain the concentration of said alkali and/or alkaline earth metal in the catalyst solution. The catalyst solution of reduced corrosion metal contaminant content is then recovered.

U.S. Pat. No. 5,466,876, herein incorporated by reference, teaches that corrosion metal contaminants are removed from a liquid composition comprising a carboxylic acid and/or an anhydride thereof, a rhodium carbonylation catalyst, and a carbonylation catalyst co-promoter by using a chelating resin selective for the removal of corrosion metals rather than carbonylation catalyst and co-promoter. Additional methods of removing corrosion metal contaminants are also disclosed in U.S. Pat. Nos. 4,985,383 and 5,124,290.

U.S. Pat. No. 4,894,477, herein incorporated by reference, teaches the use of a cation exchange resin in the lithium form to remove metallic corrosion products from a carbonylation catalyst solution which contains a rhodium component and a lithium component. The process described in U.S. Pat. No. '477 is particularly applicable to those processes which are useful for the carbonylation of methanol to acetic acid under low water conditions, such as those set forth in U.S. Pat. No. 5,001,259. U.S. Pat. No. '477 further teaches that while low water conditions improve the acetic acid purification/production process, as lithium concentrations in the low water conditions carbonylation reactor are increased to increase rhodium stability and as the water levels in the reaction system are decreased, the capacity of the ion exchange corrosion metal removal process per cycle is diminished.

Similarly, U.S. Pat. No. 5,731,252, herein incorporated by reference, teaches a process for treating low water content carbonylation catalyst solutions which contain a rhodium component and an alkali metal component to remove metallic corrosion products. The process comprises contacting the catalyst solution with an ion exchange resin, preferably in the lithium form, and a sufficient amount of water to decrease the concentration of alkali metal ions to optimize removal of corrosion metal products.

While the above-described processes have been successful in generally removing some corrosion metals using an ion exchange resin, the need exists for improving acetic acid yield by setting an iron threshold and removing iron when it is above the threshold.

SUMMARY OF THE INVENTION

This invention relates to processes for the production of acetic acid. In one embodiment, the present invention is directed to a process for producing acetic acid comprising carbonylating at least one member selected from the group consisting of methanol, dimethyl ether, and methyl acetate in a reactor in a reaction medium comprising water, a rhodium catalyst, methyl iodide and a halide salt, wherein the rhodium catalyst is present in the reaction medium in an amount from 200 to 3000 wppm as rhodium; separating a portion of the reaction medium in a flash vessel to form a less volatile stream and a vapor product stream comprising acetic acid; recycling a liquid stream to the reactor, wherein the liquid stream comprises a portion of the less volatile stream and wherein the liquid stream comprises iron; and removing a portion of the iron from the liquid stream to maintain an effective Space Time Yield (STY) of the rhodium catalyst of at least 80% of the maximum STY, e.g., at least 90% of the maximum STY. In one embodiment, the liquid stream, after removal of iron, comprises iron in an amount from 1 to 1200 wppm. Also, at least 5% of the iron may be removed from the liquid recycle. The process further maintains an iron concentration in the reaction medium of no more than 1200 wppm, and in one embodiment from 100 to 500 wppm. The iron concentration in wppm is maintained to be less than the concentration of the rhodium catalyst in wppm. In one embodiment, the process further comprises maintaining at least 85% of the rhodium needed for the effective Space Time Yield to achieve 100% of the maximum STY. In one embodiment, the less volatile stream comprises acetic acid in an amount from 60 to 90 wt. %, rhodium catalyst in an amount from 0.01 to 0.5 wt. % as rhodium, corrosion metals in a total amount from 10 to 2500 wppm, lithium iodide in an amount from 5 to 20 wt. %, methyl iodide in an amount from 1 to 25 wt. % (e.g. from 1 to 5 wt. %), methyl acetate in an amount from 0.1 to 5 wt. %, and water in an amount from 0.1 to 8 wt. %. In one embodiment, the material of the reactor and/or flasher, and the respective associated fittings and various lines, comprises a transition metal or transition-metal-based alloy. In one embodiment, the process further comprises separating the vapor product stream comprising acetic acid in a primary purification train to obtain an acetic acid product and one or more recycle streams. The liquid stream may comprise a portion of the one or more recycle streams. In addition, at least one of the one or more recycle streams comprises iron. In one embodiment, the process further comprises directing at least one stream to a permanganate reducing compound removal system to obtain a stream enriched in acetaldehyde. The reaction medium may comprise acetaldehyde in an amount of no more than 1500 wppm. In one embodiment, iron is removed from the liquid stream by contacting a portion of the liquid stream with a cation exchange resin.

In another embodiment, the present invention is directed to a process for producing acetic acid comprising carbonylating at least one member selected from the group consisting of methanol, dimethyl ether, and methyl acetate in a reactor in a reaction medium comprising a rhodium catalyst, methyl iodide and a halide salt, wherein the rhodium catalyst is present in the reaction medium in an amount from 200 to 3000 wppm as rhodium, separating a portion of the reaction medium in a flash vessel to form a less volatile stream and a vapor product stream comprising acetic acid, recycling a liquid stream to the reactor, wherein the liquid stream comprises a portion of the less volatile stream and wherein the liquid stream comprises iron, and removing a portion of the iron from the liquid stream to maintain an iron concentration in the reaction medium of no more than 1200 wppm, and in one embodiment from 100 to 500 wppm. The iron concentration in wppm may be maintained to be less than the concentration of the rhodium catalyst in wppm. In one embodiment, the process further comprises directing at least one stream to a permanganate reducing compound removal system to obtain a stream enriched in acetaldehyde. The reaction medium may comprise acetaldehyde in an amount of no more than 1500 wppm. In one embodiment, iron is removed from the liquid stream by contacting a portion of the liquid stream with a cation exchange resin. The less volatile stream comprises acetic acid in an amount from 60 to 90 wt. %, rhodium catalyst in an amount from 0.01 to 0.5 wt. % as rhodium, corrosion metals in a total amount from 10 to 2500 wppm, lithium iodide in an amount from 5 to 20 wt. %, methyl iodide in an amount from 1 to 25 wt. % (e.g., from 1 to 5 wt. %), methyl acetate in an amount from 0.1 to 5 wt. %, and water in an amount from 0.1 to 8 wt. %.

In yet another embodiment, the present invention is directed to a process for producing acetic acid comprising carbonylating at least one member selected from the group consisting of methanol, dimethyl ether, and methyl acetate in a reaction medium comprising water, a rhodium catalyst, methyl iodide and a halide salt, wherein the reaction medium comprises water in an amount from 0.1 to 14 wt. %, separating a portion of the reaction medium in a flash vessel to form a less volatile stream and a vapor product stream comprising acetic acid, recycling a liquid stream to the reactor, wherein the liquid stream comprises a portion of the less volatile stream, setting a threshold value of iron for the portion of the reaction medium, wherein the threshold value of iron concentration is a value selected within the range from 500 wppm to 1200 wppm, determining an iron content in the portion of the reaction medium, and removing at least a portion of the iron from the liquid stream when the iron content exceeds threshold value. In one embodiment, the process further comprises directing at least one stream to a permanganate reducing compound removal system to obtain a stream enriched in acetaldehyde. The reaction medium may comprise acetaldehyde in an amount of no more than 1500 wppm. In one embodiment, iron is removed from the liquid stream by contacting a portion of the liquid stream with a cation exchange resin. The less volatile stream comprises acetic acid in an amount from 60 to 90 wt. %, rhodium catalyst in an amount from 0.01 to 0.5 wt. % as rhodium, corrosion metals in a total amount from 10 to 2500 wppm, lithium iodide in an amount from 5 to 20 wt. %, methyl iodide in an amount from 1 to 25 wt. % (e.g., from 1 to 5 wt. %), methyl acetate in an amount from 0.1 to 5 wt. %, and water in an amount from 0.1 to 8 wt. %. In one embodiment, the process may further comprise separating the vapor product stream comprising acetic acid in a primary purification train to obtain an acetic acid product and one or more recycle streams. The liquid stream may comprises a portion of the one or more recycle streams. In one embodiment, the process further comprises determining an iron content in the portion of the one or more recycle streams, and removing at least a portion of the iron from the portion of the one or more recycle streams when the iron content exceeds the threshold value.

Further embodiments provide a process for producing acetic acid comprising carbonylating at least one member selected from the group consisting of methanol, dimethyl ether, and methyl acetate in a reaction medium comprising water, a rhodium catalyst, methyl iodide and a halide salt, wherein the reaction medium comprises from 0.1 to 14 wt. % water, determining an iron content in a portion of the reaction medium, separating the reaction medium into a less volatile stream comprising iron and a vapor product stream, and removing at least a portion of the iron from the less volatile stream when the iron content in the reaction medium exceeds 1200 wppm.

In a further embodiment, a process is provided for improving the productivity of a less volatile stream comprising a set water and alkali metal ion concentration and greater than 1200 ppm iron, wherein the process comprises contacting the less volatile stream in a contacting cycle with a cation exchange resin and water in an amount sufficient to bring the water concentration of the less volatile stream as it proceeds through the contacting cycle within a range of 0.25 to 50 wt. %.

In a further embodiment, a process is provided for improving the productivity of a less volatile stream employed under low water conditions, said solution containing rhodium and alkali metal and further containing greater than 1200 ppm iron, wherein the process comprises contacting the less volatile stream with an ion exchange resin and water in an amount sufficient to bring the water concentration of the less volatile stream as it proceeds through the contacting cycle within a range of 0.25 to 50 wt. % and, recover a stream comprising less than 1200 ppm iron.

BRIEF DESCRIPTION OF THE DRAWINGS

The present invention will be better understood in view of the appended non-limiting figures, wherein.

DETAILED DESCRIPTION OF THE INVENTION

Figure 1:
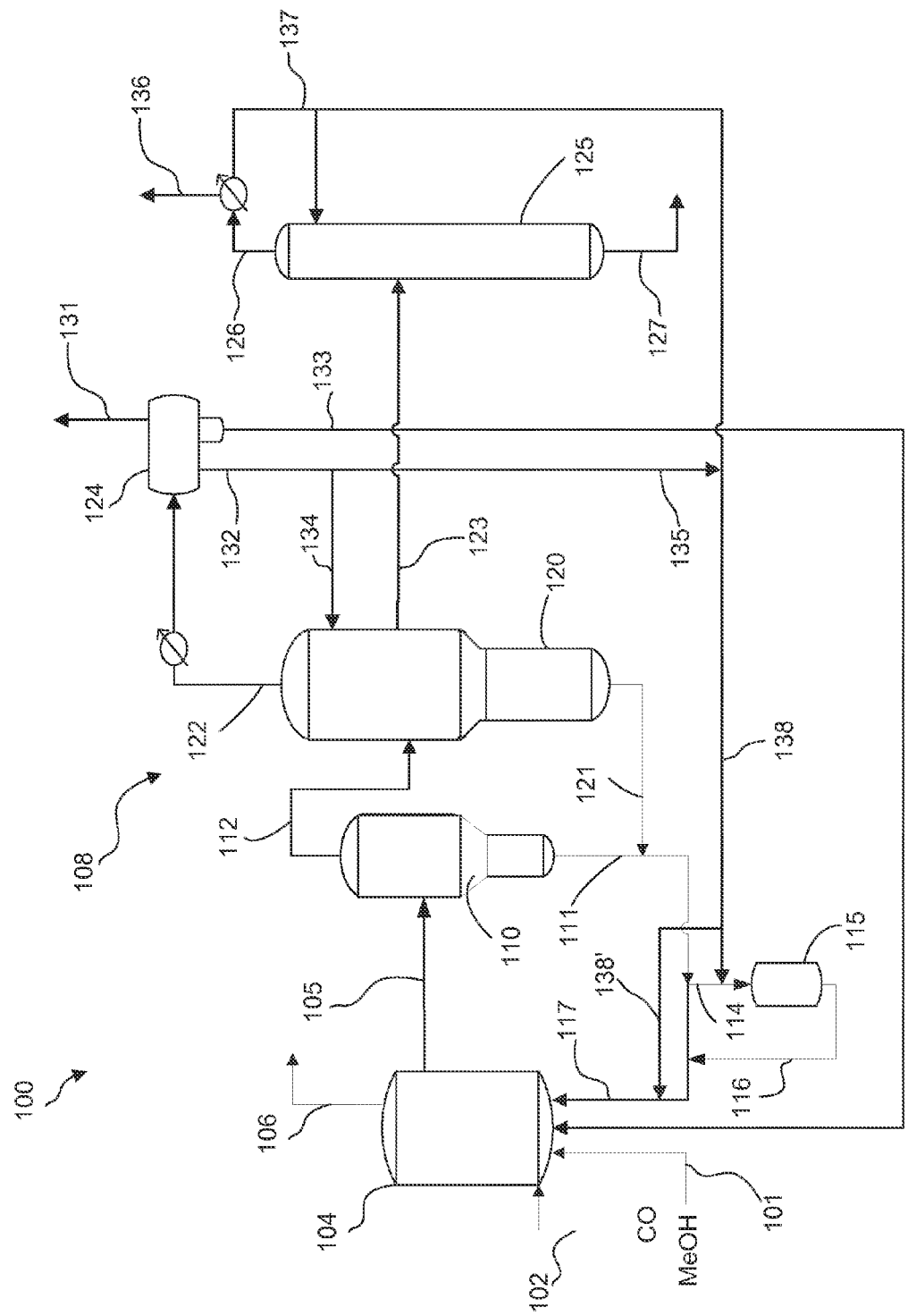
FIG. 1 illustrates an exemplary carbonylation scheme.

At the outset, it should be noted that in the development of any such actual embodiment, numerous implementation—specific decisions must be made to achieve the developer's specific goals, such as compliance with system related and business-related constraints, which will vary from one implementation to another. In addition, the processes disclosed herein can also comprise components other than those cited or specifically referred to, as is apparent to one having average or reasonable skill in the art.

In the summary and this detailed description, each numerical value should be read once as modified by the term "about" (unless already expressly so modified), and then read again as not so modified unless otherwise indicated in context. Also, in the summary and this detailed description, it should be understood that a concentration range listed or described as being useful, suitable, or the like, is intended that any and every concentration within the range, including the end points, is to be considered as having been stated. For example, a range "from 1 to 10" is to be read as indicating each and every possible number along the continuum between about 1 and about 10. Thus, even if specific data points within the range, or even no data points within the range, are explicitly identified or refer to only a few specific data points, it is to be understood that inventors appreciate and understand that any and all data points within the range are to be considered to have been specified, and that inventors possessed knowledge of the entire range and all points within the range.

Throughout the entire specification, including the claims, the following terms have the indicated meanings unless otherwise specified.

As used in the specification and claims, "near" is inclusive of "at." The term "and/or" refers to both the inclusive "and" case and the exclusive "or" case, and is used herein for brevity. For example, a mixture comprising acetic acid and/or methyl acetate may comprise acetic acid alone, methyl acetate alone, or both acetic acid and methyl acetate.

All percentages are expressed as weight percent (wt. %), based on the total weight of the particular stream or composition present, unless otherwise noted. Room temperature is 25° C. and atmospheric pressure is 101.325 kPa unless otherwise noted.

For purposes herein: acetic acid may be abbreviated as "AcOH";
   acetaldehyde may be abbreviated as "AcH";
   methyl acetate may be abbreviated "MeAc";
   methanol may be abbreviated "MeOH";
   methyl iodide may be abbreviated as "MeI";
   hydrogen iodide may be abbreviated as "HI";
   carbon monoxide may be abbreviated "CO"; and
   dimethyl ether may be abbreviated "DME".

HI refers to either molecular hydrogen iodide or dissociated hydriodic acid when at least partially ionized in a polar medium, typically a medium comprising at least some water. Unless otherwise specified, the two are referred to interchangeably. Unless otherwise specified, HI concentration is determined via acid-base titration using a potentiometric end point. In particular, HI concentration is determined via titration with a standard lithium acetate solution to a potentiometric end point. It is to be understood that for purposes herein, the concentration of HI is not determined by subtracting a concentration of iodide assumed to be associated with a measurement of corrosion metals or other non H+ cations from the total ionic iodide present in a sample.

It is to be understood that HI concentration does not refer to iodide ion concentration. HI concentration specifically refers to HI concentration as determined via potentiometric titration.

This subtraction method is an unreliable and imprecise method to determine relatively lower HI concentrations (i.e., less than about 5 weight percent) due to the fact that it assumes all non-H+ cations (such as cations of Fe, Ni, Cr, Mo) are associated with iodide anion exclusively. In reality, a significant portion of the metal cations in this process can be associated with acetate anion. Additionally, many of these metal cations have multiple valence states, which adds even more unreliability to the assumption on the amount of iodide anion which could be associated with these metals. Ultimately, this method gives rise to an unreliable determination of the actual HI concentration, especially in view of the ability to perform a simple titration directly representative of the HI concentration.

For purposes herein, an "overhead" or "distillate" of a distillation column refers to at least one of the lower boiling condensable fractions which exits at or near the top, (e.g., proximate to the top), of the distillation column, and/or the condensed form of that stream or composition. Obviously, all fractions are ultimately condensable, yet for purposes herein, a condensable fraction is condensable under the conditions present in the process as readily understood by one of skill in the art. Examples of noncondensable fractions may include nitrogen, hydrogen, and the like. Likewise, an overhead stream may be taken just below the upper most exit of a distillation column, for example, wherein the lowest boiling fraction is a non-condensable stream or represents a de-minimis stream, as would be readily understood by one of reasonable skill in the art.

The "bottoms" or "residuum" of a distillation column refers to one or more of the highest boiling fractions which exit at or near the bottom of the distillation column, also referred to herein as flowing from the bottom sump of the column. It is to be understood that a residuum may be taken from just above the very bottom exit of a distillation column, for example, wherein the very bottom fraction produced by the column is a salt, an unusable tar, a solid waste product, or a de-minimis stream as would be readily understood by one of reasonable skill in the art.

For purposes herein, distillation columns comprise a distillation zone and a bottom sump zone. The distillation zone includes everything above the bottom sump zone, i.e., between the bottom sump zone and the top of the column. For purposes herein, the bottom sump zone refers to the lower portion of the distillation column in which a liquid reservoir of the higher boiling components is present (e.g., the bottom of a distillation column) from which the bottom or residuum stream flows upon exiting the column. The bottom sump zone may include reboilers, control equipment, and the like.

It is to be understood that the term "passages", "flow paths", "flow conduits", and the like in relation to internal components of a distillation column are used interchangeably to refer to holes, tubes, channels, slits, drains, and the like, which are disposed through and/or which provide a path for liquid and/or vapor to move from one side of the internal component to the other side of the internal component. Examples of passages disposed through a structure such as a liquid distributor of a distillation column include drain holes, drain tubes, drain slits, and the like, which allow a liquid to flow through the structure from one side to another.

Average residence time is defined as the sum total of all liquid volume hold-up for a given phase within a distillation zone divided by the average flow rate of that phase through the distillation zone. The hold-up volume for a given phase can include liquid volume contained in the various internal components of the column including collectors, distributors and the like, as well as liquid contained on trays, within downcomers, and/or within structured or random packed bed sections.

Effective Space Time Yield (STY) of Rhodium Catalyst

The present invention relates to processes for producing acetic acid by maintaining corrosion metal content, such as iron, nickel, chromium, or molybdenum, to reduce the adverse effect on an effective STY of the rhodium catalyst. Although operating the reaction in equipment that is corrosion resistant and reducing the corrosion contributing compounds, such as hydrogen iodide, may help reduce corrosion metals, eventually in a continuous process corrosion metals build up in the reaction medium. In particular iron without being bound by theory is believed to have an adverse effect on the effective STY of the rhodium catalyst. This adverse effect may be the result of poisoning the rhodium catalyst or deactivation of the rhodium catalyst. Maximum STY refers to the acetic acid space time yield (STY) that would be achieved without any poisoning or deactivation of the rhodium catalysts. The effective STY is measured by acetic acid STY in the carbonylation reaction when there is poisoning the rhodium catalyst or deactivation of the rhodium catalyst. Advantageously it is desirable to operate the process with an effective STY near the maximum STY.

In one embodiment, there is provided a process for producing acetic acid comprising carbonylating at least one member selected from the group consisting of methanol, dimethyl ether, and methyl acetate in a reactor in a reaction medium comprising water, a rhodium catalyst, methyl iodide and a halide salt, wherein the rhodium catalyst is present in an amount from 200 to 3000 wppm as rhodium, separating a portion of the reaction medium in a flash vessel to form a less volatile stream and a vapor product stream comprising acetic acid, recycling a liquid stream to the reactor, wherein the liquid stream comprises a portion of the less volatile stream and wherein the liquid stream comprises iron, and removing a portion of the iron from the liquid stream to maintain an effective STY of the rhodium catalyst of at least 80% of the maximum STY, e.g., at least 85%, at least 90%, at least 95%, or at least 97%.

Acetic acid STY is expressed in gram-moles of acetic acid produced per hour per liter of the reaction medium contained in the carbonylation reactor, and may be greater than or equal to 5 mol/L/h, e.g., greater than or equal to 10 mol/L/h, greater than or equal to 12 mol/L/h, greater than or equal to 15 mol/L/h, or greater than or equal to 20 mol/L/h. In terms of ranges, the acetic acid STY may be from 5 to 50 mol/L/h, e.g., from 10 to 40 mol/L/h, from 10 to 35 mol/L/h, from 12 to 30 mol/L/h, from 12 to 28 mol/L/h, or from 12 to 25 mol/L/h. In an exemplary embodiment, the maximum STY may be 15 mol/L/h and the process may remove a portion of the iron from the liquid stream to maintain an effective STY of the rhodium catalyst that is at least 12 mol/L/h, e.g., at least 80% of the maximum STY. In one embodiment, there is provided a process for producing acetic acid comprising carbonylating at least one member selected from the group consisting of methanol, dimethyl ether, and methyl acetate in a reactor in a reaction medium comprising water, a rhodium catalyst, methyl iodide and a halide salt, separating a portion of the reaction medium in a flash vessel to form a less volatile stream and a vapor product stream comprising acetic acid, recycling a liquid stream to the reactor, wherein the liquid stream comprises a portion of the less volatile stream and wherein the liquid stream comprises iron, and removing a portion of the iron from the liquid stream to maintain an effective STY of the rhodium catalyst from 5 to 50 mol/L/h, provided that the effective STY is at least 80% of the maximum STY e.g., at least 85%, at least 90%, at least 95%, or at least 97%.

When the effective STY is less than the maximum STY the carbonylation process may be adjusted by increasing the amount of rhodium to achieve 100% of the maximum STY. Rhodium is loaded into the reactor at a loading amount from 200 wppm to 3000 wppm as rhodium. As rhodium becomes deactivated more rhodium is added so that the effective STY is close to 100% of the maximum STY. Although this increases the effective STY, there are significant capital costs associated with replacing the rhodium catalyst to compensate for the deactivation caused by excessive iron in the reaction medium. In addition, without controlling the iron concentration, the carbonylation process may require ever increasing amounts of rhodium to replace the deactivated rhodium catalyst. This becomes highly inefficient, especially when the effective STY is less than 80% of the maximum STY. As a result, the embodiments of the present invention are able to reduce the amount of rhodium that is needed to be added by maintaining iron levels in the reaction medium. In one embodiment, the process comprises maintaining at least 85% of the rhodium needed for the effective STY to achieve 100% of the maximum STY. More preferably, maintaining at least 90% of the rhodium, e.g., at least 92% of the rhodium or at least 95% of the rhodium. In an exemplary embodiment, the loading of rhodium may be 1000 wppm and the present invention reduces the amount of rhodium that is needed to achieve an effective STY that is at least 97% of the maximum STY, and thus less than 150 wppm of rhodium is added to maintain the maximum STY. In one embodiment, there is provided a process for producing acetic acid comprising carbonylating at least one member selected from the group consisting of methanol, dimethyl ether, and methyl acetate in a reactor in a reaction medium comprising water, a rhodium catalyst, methyl iodide and a halide salt, wherein the rhodium catalyst is loaded a concentration from 200 to 3000 wppm as rhodium, separating a portion of the reaction medium in a flash vessel to form a less volatile stream and a vapor product stream comprising acetic acid, recycling a liquid stream to the reactor, wherein the liquid stream comprises a portion of the less volatile stream and wherein the liquid stream comprises iron, removing a portion of the iron from the liquid stream, and maintaining at least 85% of the rhodium needed for the effective STY to achieve 100% of the maximum STY. Advantageously, reducing deactivation caused by iron may prolong rhodium catalyst life reduces overall catalyst expenditure.

Although it has been generally disclosed in the art that corrosion metals such as iron, nickel, chromium, nickel and molybdenum may adversely affect the rate at which acetic acid is produced and the overall stability of the process, the effect of iron on acetic acid yield at specific levels in the reaction medium (or liquid stream that is recycled to the reactor) has not been fully explored or understood. It has now surprisingly and unexpectedly been discovered that the effect of iron on acetic acid STY and metal catalyst deactivation is much greater than previously expected, as compared to other corrosion metals, e.g., nickel, chromium and molybdenum. Further, in one embodiment, it has been discovered that by monitoring iron content and removing iron when it reaches a threshold level, acetic acid STY loss is minimized. Thus, because the iron content is monitored and removal is only triggered when the iron content reaches a certain threshold level, the iron removal step is preferably used on demand, resulting in cost savings as compared to existing corrosion metal removal processes. For purposes of the present invention, the iron content may be measured in the reactor or in the liquid stream that is recycled to the reactor. The liquid stream may comprise a portion of the less volatile stream from the flash vessel and one or more recycle streams from the primary purification train. Iron concentrations in the liquid stream may be measured when measuring the iron in the reactor is difficult.

The threshold level may be set to achieve an iron concentration in the reaction medium that leads to less deactivation and poisoning. Setting the threshold level too low may cause the iron removal step to operate too frequently causing exhaustion of the cation exchange resin. Conversely, setting the threshold level too high may cause higher levels of iron to build up in the reaction medium and leads to further decreases in effective STY. In one embodiment, the threshold value of iron concentration is a value selected within the range from 500 wppm to 1200 wppm. Preferably iron concentrations in the reaction medium are lower than the threshold value. For example, when the threshold value is 1200 wppm, the iron concentration in the reaction medium is less than 1200 wppm, e.g., from 1 to 1200 wppm. In another exemplary embodiment, a low threshold of 500 wppm may be desired to maintain iron concentrations in the reaction medium of less than 500 wppm, e.g., from 1 to 500 wppm. In one embodiment, there is provided a process for producing acetic acid comprising carbonylating at least one member selected from the group consisting of methanol, dimethyl ether, and methyl acetate in a reaction medium comprising water in a concentration from 0.1 to 14 wt. %, a rhodium catalyst, methyl iodide and a halide salt, separating a portion of the reaction medium in a flash vessel to form a less volatile stream and a vapor product stream comprising acetic acid, recycling a liquid stream to the reactor, wherein the liquid stream comprises a portion of the less volatile stream, setting a threshold value of iron for the portion of the reaction medium, wherein the threshold value of iron concentration is a value selected within the range from 500 wppm to 1200 wppm, determining an iron content in the portion of the reaction medium, and removing at least a portion of the iron from the liquid stream when the iron content exceeds the threshold value. Advantageously, setting a threshold value and removing iron in excess of the threshold value may reduce deactivation caused by iron and thus maintain an effective STY of the rhodium catalyst at a level that is at least 80% of the maximum STY, e.g., at least 85%, at least 90%, at least 95%, or at least 97%.

Acetic Acid Production Systems

An exemplary acetic acid production process is described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The purification processes described herein may be useful in carbonylation processes that use methanol and/or methyl acetate (MeAc), methyl formate or dimethyl ether, or mixtures thereof, to produce acetic acid in the presence of a Group VIII metal catalyst, such as rhodium, and a halogen-containing catalyst promoter. A particularly useful process is the low water rhodium-catalyzed carbonylation of methanol to acetic acid as exemplified in U.S. Pat. No. 5,001,259. Other metal catalysts, e.g., iridium-based catalysts, are contemplated as well.

Generally, the metal component, e.g., the rhodium component, of the catalyst system is believed to be present in the form of a coordination compound of rhodium with a halogen component providing at least one of the ligands of such a coordination compound. In addition to the coordination of rhodium and halogen, it is also believed that carbon monoxide coordinates with rhodium. The rhodium component of the catalyst system may be provided by introducing into the reaction zone rhodium in the form of rhodium metal, rhodium salts such as the oxides, acetates, iodides, carbonates, hydroxides, chlorides, etc., or other compounds that result in the formation of a coordination compound of rhodium in the reaction environment.

The metal catalyst may comprise a Group VIII metal. Suitable Group VIII catalysts include rhodium and/or iridium catalysts. When a rhodium catalyst is used, the rhodium catalyst may be added in any suitable form such that rhodium is in the catalyst solution as an equilibrium mixture including $[Rh(CO)_2I_2]$-anion, as is well known in the art. Iodide salts optionally maintained in the reaction mixtures of the processes described herein may be in the form of a soluble salt of an alkali metal or alkaline earth metal, quaternary ammonium, phosphonium salt or mixtures thereof. In certain embodiments, the catalyst co-promoter is lithium iodide, lithium acetate, or mixtures thereof. The salt co-promoter may be added as a non-iodide salt that generates an iodide salt. The iodide catalyst stabilizer may be introduced directly into the reaction system. Alternatively, the iodide salt may be generated in-situ since under the operating conditions of the reaction system, a wide range of non-iodide salt precursors reacts with methyl iodide or hydroiodic acid in the reaction medium to generate the corresponding co-promoter iodide salt stabilizer. For additional detail regarding rhodium catalysis and iodide salt generation, see U.S. Pat. Nos. 5,001,259; 5,026,908; 5,144,068 and 7,005,541, the entireties of which are hereby incorporated by reference. The carbonylation of methanol utilizing iridium catalyst is well known and is generally described in U.S. Pat. Nos. 5,942,460, 5,932,764, 5,883,295, 5,877,348, 5,877,347 and 5,696,284, the entireties of which are hereby incorporated by reference.

The halogen-containing catalyst promoter of the catalyst system consists of a halogen compound comprising an organic halide. Thus, alkyl, aryl, and substituted alkyl or aryl halides can be used. Preferably, the halogen-containing catalyst promoter is present in the form of an alkyl halide. Even more preferably, the halogen-containing catalyst promoter is present in the form of an alkyl halide in which the alkyl radical corresponds to the alkyl radical of the feed alcohol, which is being carbonylated. Thus, in the carbonylation of methanol to acetic acid, the halide promoter may include methyl halide, and more preferably methyl iodide.

The reaction medium contains the rhodium catalyst in an amount from 200 to 3000 wppm as rhodium, e.g., from 500 to 2000 wppm, or from 600 to 1500 wppm. To prevent the deactivation of the rhodium the present invention reduces the iron concentration in the reaction medium to a concentration that is less than the rhodium catalyst. When the iron concentration exceeds the rhodium catalyst concentration the adverse effect on catalyst deactivation accelerates. Thus, in one embodiment, there is provided a process for producing acetic acid comprising carbonylating at least one member selected from the group consisting of methanol, dimethyl ether, and methyl acetate in a reaction medium comprising water, a rhodium catalyst, methyl iodide and a halide salt, wherein the rhodium catalyst concentration in the reaction medium is in an amount from 200 to 3000 wppm as rhodium; and maintaining an iron concentration in the reaction medium that is less than the rhodium catalyst concentration.

In embodiments, the iron concentration in the reaction medium is maintained to be no more than 1200 wppm, e.g., no more than 1100 wppm, no more than 1000 wppm, no more than 900 wppm, no more than 800 wppm, no more than 700 wppm, no more than 600 wppm, no more than 500 wppm, no more than 400 wppm, or no more than 300 wppm, and/or the iron concentration in the reaction medium is maintained to be greater than or equal to 0 wppm, e.g., greater than or equal to 1 wppm, greater than or equal to 5 wppm, greater than or equal to 25 wppm, greater than or equal to 50 wppm, greater than or equal to 100 wppm, greater than or equal to 200 wppm, greater than or equal to 300 wppm or greater than or equal to 400 wppm. In one embodiment, there is provided a process for producing acetic acid comprising carbonylating at least one member selected from the group consisting of methanol, dimethyl ether, and methyl acetate in a reactor in a reaction medium comprising water, a rhodium catalyst, methyl iodide and a halide salt, wherein the rhodium catalyst is present in an amount from 200 to 3000 wppm as rhodium, separating a portion of the reaction medium in a flash vessel to form a less volatile stream and a vapor product stream comprising acetic acid, recycling a liquid stream to the reactor, wherein the liquid stream comprises a portion of the less volatile stream and wherein the liquid stream comprises iron, and removing a portion of the iron from the liquid stream to maintain an iron concentration in the reaction medium of no more than 1200 wppm.

As described herein controlling the concentration of iron in the reaction medium is advantageous to prevent further deactivation of the rhodium catalyst. In some embodiments, there may be other corrosion metals that accumulate in the reaction medium. These corrosion metals include nickel, molybdenum, and chromium. In one embodiment, the total concentration of nickel, molybdenum, and chromium is less than the iron concentration in the reaction medium. In embodiments, the total concentration of nickel, molybdenum, and chromium in the reaction is maintained to be no more than 800 wppm, e.g., no more than 700 wppm, no more than 600 wppm, no more than 500 wppm, no more than 400 wppm, no more than 300 wppm, no more than 200 wppm, or no more than 100 wppm, and/or the total concentration of nickel, molybdenum, and chromium in the reaction is maintained to be greater than or equal to 0 wppm, e.g., greater than or equal to 1 wppm, greater than or equal to 5 wppm, greater than or equal to 10 wppm, greater than or equal to 20 wppm, greater than or equal to 25 wppm, greater than or equal to 50 wppm, greater than or equal to 300 wppm or greater than or equal to 100 wppm. In some embodiments, the total corrosion metal concentration, including iron, nickel, molybdenum, and chromium, in the reaction medium may be from 10 to 2500 wppm, e.g., from 20 to 2000 wppm, from 50 to 1500 wppm, from 50 to 1000 wppm, or from 50 to 500 wppm.

In one embodiment, there is provided a process for producing acetic acid comprising carbonylating at least one member selected from the group consisting of methanol, dimethyl ether, and methyl acetate in a reactor in a reaction medium comprising water, a rhodium catalyst, methyl iodide and a halide salt, wherein the rhodium catalyst is present in an amount from 200 to 3000 wppm as rhodium, separating a portion of the reaction medium in a flash vessel to form a less volatile stream and a vapor product stream comprising acetic acid, recycling a liquid stream to the reactor, wherein the liquid stream comprises a portion of the less volatile stream and wherein the liquid stream comprises one or more corrosion metals selected from the group consisting of iron, nickel, molybdenum, chromium, and mixtures thereof, and removing a portion of the one or more corrosion metals from the liquid stream to maintain a total corrosion metal concentration in the reaction medium from 10 to 2500 wppm. In a preferred embodiment, iron concentration in the reaction medium is maintained to be no more than 1200 wppm.

In addition to the rhodium catalyst and iron concentration, the other components of the reaction medium are maintained within defined limits to ensure sufficient production of acetic acid. The concentration of water in the reaction medium is maintained to be no more than 14 wt. %, e.g., from 0.1 wt. % to 14 wt. %, from 0.2 wt. % to 10 wt. % or from 0.25 wt. % to 5 wt. %. Preferably, the reaction is conducted under low water conditions and the reaction medium contains water in an amount from 0.1 to 4.1 wt. %, e.g., from 0.1 to 3.1 wt. % or from 0.5 to 2.8 wt. %. The concentration of methyl iodide in the reaction medium is maintained to be from 1 to 25 wt. %, e.g., from 5 to 20 wt. %, from 4 to 13.9 wt. %. The concentration of iodide salt, e.g., lithium iodide, in the reaction medium is maintained to be from 1 to 25 wt. %, e.g., from 2 to 20 wt. %, from 3 to 20 wt. %. The concentration of methyl acetate in the reaction medium is maintained to be from 0.5 to 30 wt. %, e.g., from 0.3 to 20 wt. %, from 0.6 to 4.1 wt. %. The following amounts are based on the total weight of the reaction medium. The concentration of acetic acid in the reaction medium is greater than or equal to 30 wt. %, e.g., greater than or equal to 40 wt. %, greater than or equal to 50 wt. %, or greater than or equal to 60 wt. %. The concentration of acetaldehyde in the reaction medium is preferably maintained to be in low concentrations and in one embodiment the acetaldehyde concentration is in an amount of no more than 1500 wppm, e.g., no more than 1200 wppm, no more than 1000 wppm, no more than 900 wppm, no more than 800 wppm, no more than 700 wppm, no more than 600 wppm, no more than 500 wppm, or no more than 400 wppm. Accordingly, there is provided a process for producing acetic acid comprising carbonylating at least one member selected from the group consisting of methanol, dimethyl ether, and methyl acetate in a reactor in a reaction medium comprising water, a rhodium catalyst, methyl iodide, a halide salt, and acetaldehyde, wherein the acetaldehyde concentration in the reaction medium is in an amount of no more than 1500 wppm, separating a portion of the reaction medium in a flash vessel to form a less volatile stream and a vapor product stream comprising acetic acid, recycling a liquid stream to the reactor, wherein the liquid stream comprises a portion of the less volatile stream and wherein the liquid stream comprises iron, and removing a portion of the iron from the liquid stream, and preferably the iron is removed to maintain an effective STY of the rhodium catalyst of at least 80% of the maximum STY.

In embodiments, the process for producing acetic acid further includes introducing a lithium compound into the reactor to maintain the concentration of lithium acetate in an amount from 0.3 to 0.7 wt. % in the reaction medium, wherein in an exemplary embodiment, in the reaction medium the concentration of the rhodium catalyst is maintained in an amount from 200 to 3000 wppm as rhodium in the reaction medium, the concentration of water is maintained in amount from 0.1 to 4.1 wt. % in the reaction medium, and the concentration of methyl acetate is maintained from 0.6 to 4.1 wt. % in the reaction medium, based on the total weight of the reaction medium present within the carbonylation reactor.

In embodiments, the lithium compound introduced into the reactor is selected from the group consisting of lithium acetate, lithium carboxylates, lithium carbonates, lithium hydroxide, other organic lithium salts, and mixtures thereof. In embodiments, the lithium compound is soluble in the reaction medium. In an embodiment, lithium acetate dihydrate may be used as the source of the lithium compound.

Lithium acetate reacts with hydrogen iodide according to the following equilibrium reaction (I) to form lithium iodide and acetic acid:

$$\text{LiOAc} + \text{HI} \rightleftharpoons \text{LiI} + \text{HOAc} \quad (I)$$

Lithium acetate is thought to provide improved control of hydrogen iodide concentration relative to other acetates, such as methyl acetate, present in the reaction medium. Without being bound by theory, lithium acetate is a conjugate base of acetic acid and thus reactive toward hydrogen iodide via an acid-base reaction. This property is thought to result in an equilibrium of the reaction (I) which favors reaction products over and above that produced by the corresponding equilibrium of methyl acetate and hydrogen iodide. This improved equilibrium is favored by water concentrations of less than 4.1 wt. % in the reaction medium. In addition, the relatively low volatility of lithium acetate compared to methyl acetate allows the lithium acetate to remain in the reaction medium except for volatility losses and small amounts of entrainment into the vapor crude product. In contrast, the relatively high volatility of methyl acetate allows the material to distill into the purification train, rendering methyl acetate more difficult to control. Lithium acetate is much easier to maintain and control in the process at consistent low concentrations of hydrogen iodide. Accordingly, a relatively small amount of lithium acetate may be employed relative to the amount of methyl acetate needed to control hydrogen iodide concentrations in the reaction medium. It has further been discovered that lithium acetate is at least three times more effective than methyl acetate in promoting methyl iodide oxidative addition to the rhodium [I] complex. However, it has been discovered that lithium cations derived from and/or generated by the lithium compound in the reaction medium may be entrained or be volatile enough to concentrate with the crude acetic acid product after purification in the primary purification trains.

In embodiments, the concentration of lithium acetate in the reaction medium is maintained at greater than or equal to 0.3 wt. %, or greater than or equal to 0.35 wt. %, or greater than or equal to 0.4 wt. %, or greater than or equal to 0.45 wt. %, or greater than or equal to 0.5 wt. %, and/or in embodiments, the concentration of lithium acetate in the reaction medium is maintained at no more than 0.7 wt. %, or no more than 0.65 wt. %, or no more than 0.6 wt. %, or no more than 0.55 wt. %.

It has been discovered that an excess of lithium acetate in the reaction medium can adversely affect the other compounds in the reaction medium, leading to decreased productivity. Conversely, it has been discovered that a lithium acetate concentration in the reaction medium below about 0.3 wt. % is unable to maintain the desired hydrogen iodide concentrations in the reaction medium of below 1.3 wt. %.

In embodiments, the lithium compound may be introduced continuously or intermittently into the reaction medium. In embodiments, the lithium compound is introduced during reactor start up. In embodiments, the lithium compound is introduced intermittently to replace entrainment losses.

Accordingly, in one embodiment there is provided a process for producing acetic acid comprising carbonylating at least one member selected from the group consisting of methanol, dimethyl ether, and methyl acetate in a reactor in a reaction medium comprising water, a rhodium catalyst, methyl iodide, a halide salt, and lithium acetate, separating a portion of the reaction medium in a flash vessel to form a less volatile stream and a vapor product stream comprising acetic acid, recycling a liquid stream to the reactor, wherein the liquid stream comprises a portion of the less volatile stream and wherein the liquid stream comprises iron, and removing a portion of the iron from the liquid stream to maintain an effective STY of the rhodium catalyst of at least 80% of the maximum STY.

In some embodiments, the desired reaction rates are obtained even at low water concentrations by maintaining in the reaction medium an ester of the desired carboxylic acid and an alcohol, desirably the alcohol used in the carbonylation, and an additional iodide ion that is over and above the iodide ion that is present as hydrogen iodide. A desired ester is methyl acetate. The additional iodide ion is desirably an iodide salt, with lithium iodide (LiI) being preferred. It has been found, as described in U.S. Pat. No. 5,001,259, that under low water concentrations, methyl acetate and lithium iodide act as rate promoters.

The carbonylation reaction of methanol to acetic acid product may be carried out by contacting the methanol feed with gaseous carbon monoxide bubbled through an acetic acid solvent reaction medium containing the rhodium catalyst, methyl iodide promoter, methyl acetate, and additional soluble iodide salt, at conditions of temperature and pressure suitable to form the carbonylation product. It will be generally recognized that it is the concentration of iodide ion in the catalyst system that is important and not the cation associated with the iodide, and that at a given molar concentration of iodide, the nature of the cation is not as significant as the effect of the iodide concentration. Any metal iodide salt, or any iodide salt of any organic cation, or other cations such as those based on amine or phosphine compounds (optionally, ternary or quaternary cations), can be maintained in the reaction medium provided that the salt is sufficiently soluble in the reaction medium to provide the desired level of iodide. When the iodide is a metal salt, preferably it is an iodide salt of a member of the group consisting of the metals of Group IA and Group IIA of the periodic table as set forth in the "Handbook of Chemistry and Physics" published by CRC Press, Cleveland, Ohio, 2002 March (83rd edition). In particular, alkali metal iodides are useful, with lithium iodide being particularly suitable. In the low water carbonylation process, the additional iodide ion over and above the iodide ion present as hydrogen iodide is generally present in the catalyst solution in amounts such that the total iodide ion concentration is from 1 to 25 wt. % and the methyl acetate is generally present in amounts from 0.5 to 30 wt. %, and the methyl iodide is generally present in amounts from 1 to 25 wt. %. The rhodium catalyst is generally present in amounts from 200 to 3000 wppm as rhodium.

The reaction medium may also contain impurities that should be controlled to avoid byproduct formation. One impurity in the reaction medium may be ethyl iodide, which is difficult to separate from acetic acid. Applicant has further discovered that the formation of ethyl iodide may be affected by numerous variables, including the concentrations of acetaldehyde, ethyl acetate, methyl acetate and methyl iodide in the reaction medium. Additionally, ethanol content in the methanol source, hydrogen partial pressure and hydrogen content in the carbon monoxide source have been discovered to affect ethyl iodide concentration in the reaction medium and, consequently, the propionic acid concentration in the final acetic acid product.

In one embodiment there may be trace amounts of iron (wppb) in the methanol source that is present particulate matter or soluble iron in the form of rust. In addition, in the carbon monoxide feed there may be trace amounts of iron, in particular iron pentacarbonyl, that is also introduced into the reactor.

In embodiments, the propionic acid concentration in the acetic acid product may further be maintained below 250 wppm by maintaining the ethyl iodide concentration in the reaction medium at no more than 750 wppm, without removing propionic acid from the acetic acid product. In one embodiment there is provided a process for producing acetic acid comprising carbonylating at least one member selected from the group consisting of methanol, dimethyl ether, and methyl acetate in a reactor in a reaction medium comprising water, a rhodium catalyst, methyl iodide, a halide salt, and ethyl iodide, wherein the concentration of ethyl iodide is at no more than 750 wppm, separating a portion of the reaction medium in a flash vessel to form a less volatile stream and a vapor product stream comprising acetic acid, recycling a liquid stream to the reactor, wherein the liquid stream comprises a portion of the less volatile stream and wherein the liquid stream comprises iron, and removing a portion of the iron from the liquid stream to maintain an effective STY of the rhodium catalyst of at least 80% of the maximum STY.

In embodiments, the ethyl iodide concentration in the reaction medium and propionic acid in the acetic acid product may be present in a weight ratio from 3:1 to 1:2. In embodiments, the acetaldehyde:ethyl iodide concentration in the reaction medium is maintained at a weight ratio from 2:1 to 20:1.

In embodiments, the ethyl iodide concentration in the reaction medium may be maintained by controlling at least one of the hydrogen partial pressure, the methyl acetate concentration, the methyl iodide concentration, and/or the acetaldehyde concentration in the reaction medium.

In embodiments, the concentration of ethyl iodide in the reaction medium is maintained/controlled to be no more than 750 wppm, or e.g., no more than 650 wppm, or no more than 550 wppm, or no more than 450 wppm, or no more than 350 wppm. In embodiments, the concentration of ethyl iodide in the reaction medium is maintained/controlled at greater than or equal to 1 wppm, or e.g., 5 wppm, or 10 wppm, or 20 wppm, or 25 wppm, and no more than 650 wppm, or e.g., 550 wppm, or 450 wppm, or 350 wppm.

In embodiments, the weight ratio of ethyl iodide in the reaction medium to propionic acid in the acetic acid product may range from 3:1 to 1:2, or e.g., from 5:2 to 1:2, or from 2:1 to 1:2, or from 3:2 to 1:2.

In embodiments, the weight ratio of acetaldehyde to ethyl iodide in the reaction medium may range from 20:1 to 2:1, or e.g., from 15:1 to 2:1, from 9:1 to 2:1, or from 6:1.

Typical reaction temperatures for carbonylation may be from 150° C. to 250° C., e.g., from 160° C. to 240° C., from 170° C. to 230° C., and with the temperature range from 180° C. to 225° C. being a preferred range. The carbon monoxide partial pressure in the reactor can vary widely but is typically from 2 to 30 atm, e.g., from 3 to 10 atm. The hydrogen partial pressure in the reactor is typically from 0.05 to 2 atm, e.g., from 1 to 1.9 atm. In some embodiments, the present invention may be operated with a hydrogen partial pressure from 0.3 to 2 atm, e.g., from 0.3 to 1.5 atm, or from 0.4 to 1.5 atm. Because of the partial pressure of by-products and the vapor pressure of the contained liquids, the total reactor pressure may range from 15 to 40 atm. As described herein, the production rate of acetic acid, as determined by acetic acid STY, may be from 5 to 50 mol/L/h, e.g., from 10 to 40 mol/L/h, and preferably 15 to 35 mol/L/h.

Exemplary reaction and acetic acid recovery system 100 is shown in FIG. 1. As shown, methanol-containing feed stream 101 and carbon monoxide-containing feed stream 102 are directed to liquid phase carbonylation reactor 104, in which the carbonylation reaction occurs to form acetic acid.

Carbonylation reactor 104 is preferably either a stirred vessel or bubble-column type vessel, with or without an agitator, within which the reacting liquid or slurry contents are maintained, preferably automatically, a predetermined level, which preferably remains substantially constant during normal operation. Into carbonylation reactor 104, fresh methanol, carbon monoxide, and sufficient water are continuously introduced as needed to maintain suitable concentrations in the reaction medium.

The material of carbonylation reactor 104 and its associated fittings and various lines may be made of suitable materials such as glass, metal, ceramic, or combinations thereof, and is not particularly limited to a specific one. Associated fittings include but are not limited to associated piping, pumps and heat exchangers. According to the present invention, the material of the carbonylation reactor 104 and its associated fittings and various lines may be a transition metal or a transition-metal-based alloy such as iron alloy, e.g., nickel or nickel alloy, zirconium or zirconium alloy thereof, or titanium or titanium alloy thereof. Suitable iron-based alloys include those containing iron as a main component, e.g., a stainless steel that also comprises chromium, nickel, molybdenum and others. Suitable nickel-based alloys include those alloys containing nickel as a main component and one or more of chromium, iron, cobalt, molybdenum, tungsten, manganese, and others, e.g., HAS- TELLOY™ and INCONEL™. Corrosion-resistant metals may be particularly suitable as materials for carbonylation reactor 104 and its associated fittings and various lines. Even when corrosion-resistant metals are used for carbonylation reactor 104, the associated fittings and various lines of the reactor may be made of a less corrosion-resistant metal which may be the source of the corrosion metals, including iron. Accordingly, in one embodiment, there is provided a process for producing acetic acid comprising carbonylating at least one member selected from the group consisting of methanol, dimethyl ether, and methyl acetate in a reactor in a reaction medium comprising water, a rhodium catalyst, methyl iodide and a halide salt, wherein the reactor comprises a transition metal or a transition-metal-based alloy such as iron alloy, e.g., nickel or nickel alloy, zirconium or zirconium alloy thereof, or titanium or titanium alloy thereof, separating a portion of the reaction medium in a flash vessel to form a less volatile stream and a vapor product stream comprising acetic acid, recycling a liquid stream to the reactor, wherein the liquid stream comprises a portion of the less volatile stream and wherein the liquid stream comprises iron, and removing a portion of the iron from the liquid stream to maintain an effective STY of the rhodium catalyst of at least 80% of the maximum STY.

In a typical carbonylation process, carbon monoxide is continuously introduced into the carbonylation reactor, desirably below the agitator, which may be used to stir the contents. The gaseous feed preferably is thoroughly dispersed through the reacting liquid by this stirring means. Gaseous purge stream 106 desirably is vented from the reactor 104 to prevent buildup of gaseous by-products and to maintain a set carbon monoxide partial pressure at a given total reactor pressure. In one embodiment, the gaseous purge stream 106 contains low amounts of hydrogen iodide of no more than 1 wt. %, e.g., no more than 0.9 wt. %, no more than 0.8 wt. %, no more than 0.7 wt. %, no more than 0.5 wt. %, no more than 0.3 wt. %. Hydrogen iodide in excess of these amounts may increase the duty on the scrubber to prevent hydrogen iodide from being purged. The temperature of the reactor may be controlled and the carbon monoxide feed is introduced at a rate sufficient to maintain the desired total reactor pressure. Stream 105 comprising the liquid reaction medium exits reactor 104.

The acetic acid production system preferably includes primary purification train 108 employed to recover the acetic acid and recycle catalysts, methyl iodide, methyl acetate, and other system components within the process. In recycling those components however, the process may also recycle corrosion metals to the reactor 104, further contributing to the buildup of corrosion metals. Primary purification train 108 include light ends column 120 and drying column 125, and the associated pumps, overhead receivers, condensers, etc. The separation system also preferably controls water and acetic acid content in the carbonylation reactor, as well as throughout the system, and facilitates PRC removal. In one embodiment, a liquid recycle 137 comprising a portion of the less volatile stream 111 and a portion one or more recycle streams 138 from the primary purification train 108 are introduced into the reactor 104. The iron that builds up in reactor 104 may be introduced by liquid recycle 137. Thus, it is important to remove iron, in addition to other corrosion metals, from liquid recycle 137.

Flash Vessel

The reaction medium is drawn off from the carbonylation reactor 104 at a rate sufficient to maintain a constant level therein and is provided to flash vessel 110 via stream 105. In flash vessel 110, the crude product is separated in a flash separation step to obtain a vapor product stream 112 comprising acetic acid and less volatile stream 111 comprising a catalyst-containing solution (predominantly acetic acid containing the rhodium and the iodide salt along with lesser quantities of methyl acetate, methyl iodide, and water), which preferably is recycled to the reactor, as part of the liquid recycle 137. The respective flow rates of vapor product stream 112 and less volatile stream 111 may vary, and in one exemplary embodiment from 15% to 55% of the flow into flash vessel 110 is removed as vapor product stream 112, and from 45% to 85% of the flow is removed as less volatile stream 111. Corrosion metals, including iron, concentrate in the less volatile stream 111 and are returned to carbonylation reactor 104, thus causing these corrosion metals to undesirably build up in the reaction medium.

The material of flash vessel 110 and its associated fittings and various lines, each communicating to the distillation system may be made of suitable materials such as glass, metal, ceramic, or combinations thereof, and is not particularly limited to a specific one. According to the present invention, the material of the foregoing flash vessel 110 and its associated fittings and various lines may be a transition metal or a transition-metal-based alloy such as iron alloy, e.g., a stainless steel, nickel or nickel alloy, zirconium or zirconium alloy thereof, titanium or titanium alloy thereof, or aluminum alloy. Suitable iron-based alloys include those containing iron as a main component, e.g., a stainless steel that also comprises chromium, nickel, molybdenum and others. Suitable nickel-based alloys include those alloys containing nickel as a main component and one or more of chromium, iron, cobalt, molybdenum, tungsten, manganese, and others, e.g., HASTELLOY™ and INCONEL™. Corrosion-resistant metals may be particularly suitable as materials for flash vessel 110 and its associated fittings and various lines. Accordingly, in one embodiment, there is provided a process for producing acetic acid comprising carbonylating at least one member selected from the group consisting of methanol, dimethyl ether, and methyl acetate in a reactor in a reaction medium comprising water, a rhodium catalyst, methyl iodide and a halide salt, separating a portion of the reaction medium in a flash vessel to form a less volatile stream and a vapor product stream comprising acetic acid, wherein the flash vessel comprises a transition metal or a transition-metal-based alloy such as iron alloy, e.g., a stainless steel, nickel or nickel alloy, zirconium or zirconium alloy thereof, titanium or titanium alloy thereof, or aluminum alloy, recycling a liquid stream to the reactor, wherein the liquid stream comprises a portion of the less volatile stream and wherein the liquid stream comprises iron, and removing a portion of the iron from the liquid stream to maintain an effective STY of the rhodium catalyst of at least 80% of the maximum STY.

The vapor product stream 112 also comprises methyl iodide, methyl acetate, water, and permanganate reducing compounds (PRC's). Dissolved gases exiting the reactor and entering the flash vessel comprise a portion of the carbon monoxide and may also contain gaseous by-products such as methane, hydrogen, and carbon dioxide. Such dissolved gases exit the flash vessel as part of the overhead stream. In one embodiment, vapor product stream 112 comprises acetic acid, methyl iodide, methyl acetate, water, acetaldehyde, and hydrogen iodide. In one embodiment, vapor product stream 112 comprises acetic acid in an amount from 45 to 75 wt. %, methyl iodide in an amount from 20 to 50 wt. %, methyl acetate in an amount of no more than 9 wt. %, and water in an amount of no more than 15 wt. %, based on the total weight of the vapor product stream. In another embodiment, vapor product stream 112 comprises acetic acid in an amount from 45 to 75 wt. %, methyl iodide in an amount from 24 to less than 36 wt. %, methyl acetate in an amount of no more than 9 wt. %, and water in an amount of no more than 15 wt. %, based on the total weight of the vapor product stream. More preferably, vapor product stream 112 comprises acetic acid in an amount from 55 to 75 wt. %, methyl iodide in an amount from 24 to 35 wt. %, methyl acetate in an amount from 0.5 to 8 wt. %, and water in an amount from 0.5 to 14 wt. %. In yet a further preferred embodiment, vapor product stream 112 comprises acetic acid in an amount from 60 to 70 wt. %, methyl iodide in an amount from 25 to 35 wt. %, methyl acetate in an amount from 0.5 to 6.5 wt. %, and water in an amount from 1 to 8 wt. %. The acetaldehyde concentration in the vapor product stream may be in an amount from 0.005 to 1 wt. %, based on the total weight of the vapor product stream, e.g., from 0.01 to 0.8 wt. %, or from 0.01 to 0.7 wt. %. In some embodiments the acetaldehyde may be present in amounts no more than 0.01 wt. %. Vapor product stream 112 may comprise hydrogen iodide in an amount no more than 1 wt. %, based on the total weight of the vapor product stream, e.g., no more than 0.5 wt. %, or no more than 0.1 wt. %. Vapor product stream 112 is preferably substantially free of, i.e., contains no more than 0.0001 wt. %, propionic acid, based on the total weight of the vapor product stream.

Less volatile stream 111 comprises acetic acid, the rhodium catalyst, corrosion metals, as well as other various compounds. In one embodiment, less volatile stream 111 comprises acetic acid in an amount from 60 to 90 wt. %, rhodium catalyst in an amount from 0.01 to 0.5 wt. % as rhodium; corrosion metals (e.g., nickel, iron, molybdenum, and chromium) in a total amount from 10 to 2500 wppm; lithium iodide in an amount from 5 to 20 wt. %; methyl iodide in an amount from 1 to 25 wt. % (e.g., from 1 to 5 wt. %); methyl acetate in an amount from 0.1 to 5 wt. %; water in an amount from 0.1 to 8 wt. %; acetaldehyde in an amount of no more than 1 wt. % (e.g., from 0.0001 to 1 wt. % acetaldehyde); and hydrogen iodide in an amount of no more than 0.5 wt. % (e.g., from 0.0001 to 0.5 wt. % hydrogen iodide).

Iron Detection and Removal

Figure 2:
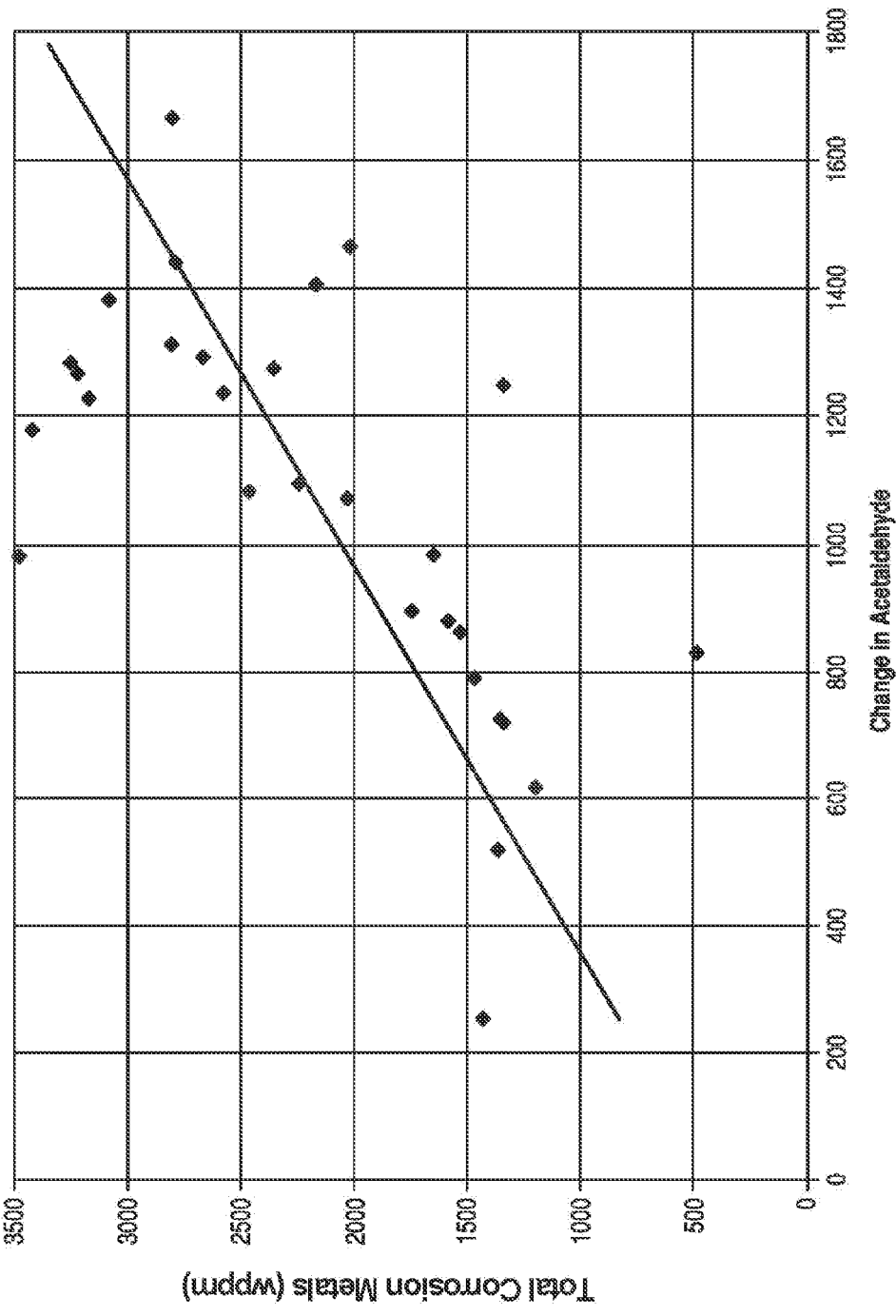
FIG. 2 illustrates the total corrosion metals concentration versus acetaldehyde concentration.
Figure 3:
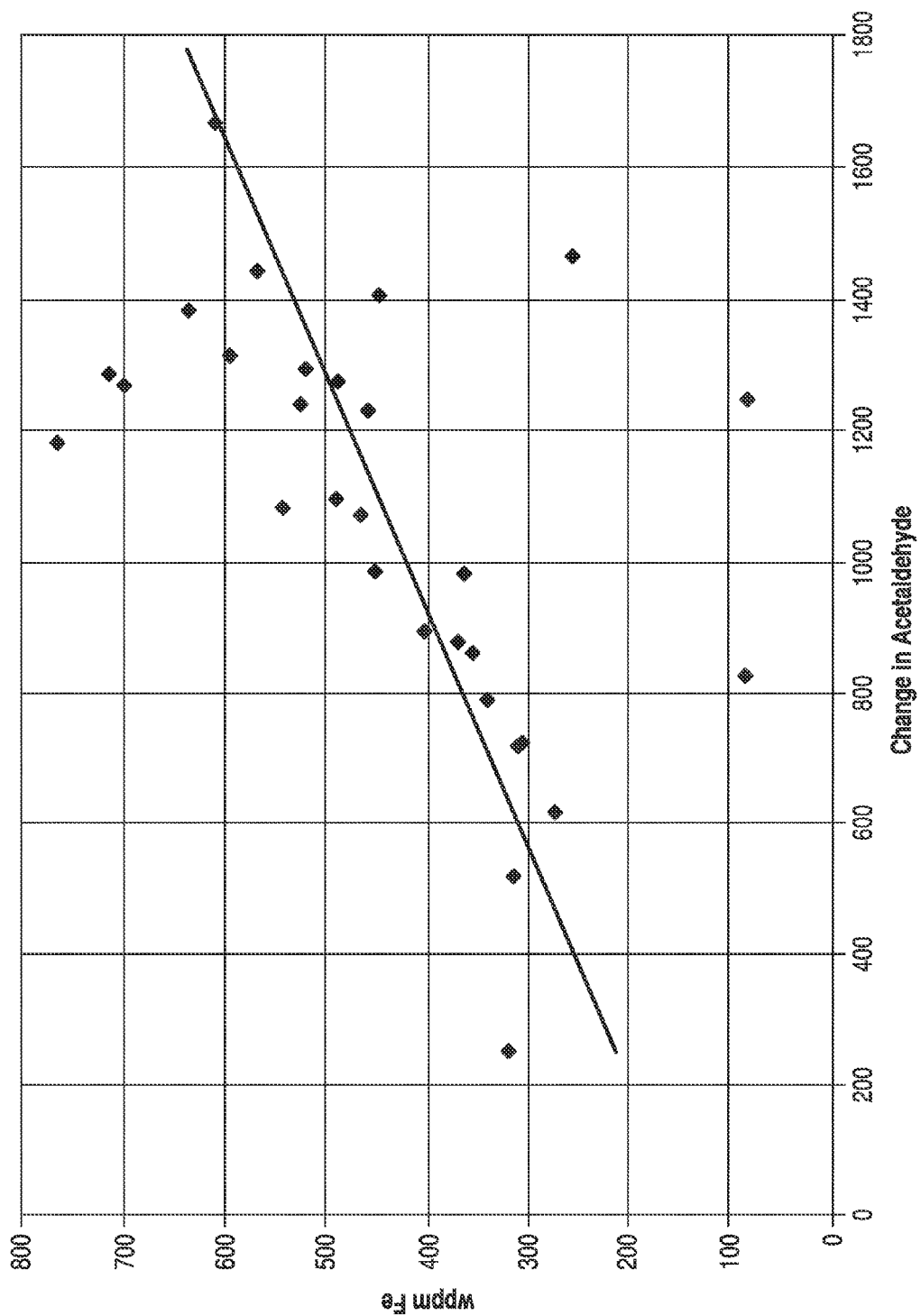
FIG. 3 illustrates the iron concentration versus acetaldehyde concentration.

As described herein, when the carbonylation reaction is run over extended periods of time, e.g., over several days, weeks, months or years, corrosion metals dissolve from the carbonylation reactor and/or flash vessel, its associated fittings and various lines, into the reaction medium, and less volatile stream 111 causing undesirable build up therein. Additionally, there are corrosion metals in the various recycle streams 138 from primary purification train 108, as described herein, that also accumulate in the reaction medium. A portion of these various recycle streams 138 are combined with a portion of the less volatile stream 111 to be treated in the corrosion metal removal unit 115. Since the process is continuous, the corrosion metals continue to build up in the reactor 104. Although the particular corrosion metals depend on the metallurgy, they commonly include iron, nickel, molybdenum and chromium. The corrosion metals are known to interfere with the carbonylation reaction, to accelerate competing reactions such as the water-gas shift reaction and methane formation, and to deactivate the rhodium catalyst. As corrosion metal concentration increases, then PRC concentration also increases in a proportional relationship. While it is recognized in the art that removal of corrosion metals is desirable, the corrosion metals are generally removed from reactor 104 to reduce total corrosion metals concentration, as opposed to targeted reduction of any one specific corrosion metal, e.g., iron. FIG. 2 is a plot of total corrosion metal concentration (reported in weight parts per million ("wppm") as compared to change in acetaldehyde concentration (wppm) in reactor 104 for a rhodium based system under low water conditions as previously described. FIG. 2 shows that as total corrosion metal concentration increases, acetaldehyde concentration increases. A similar relationship is shown in FIG. 3, where the iron concentration (wppm) is compared to the change in acetaldehyde concentration (wppm) in reactor 104. As previously described, increases in acetaldehyde content lead to purification increases, which lead to cost increases and production rate limitations. Additionally, as the total corrosion metals concentration increases, the content of other PRC's including butyraldehyde, crotonaldehyde, and 2-ethylcrotonaldehyde, as well as butyl acetate also increased. Thus, the conventional strategy to reduce total corrosion metal concentration in order to reduce PRC concentration is supported by the data in FIGS. 2 and 3.

Further evaluation of the individual corrosion metals shows that, unexpectedly, of all the corrosion metals, the presence of iron above a threshold level has a disproportionally large effect on acetic acid STY. Thus, measuring total corrosion metal concentration may not provide a reliable indicator of iron concentration. For example, FIG. 6, discussed further herein, illustrates the poisoning effect of iron on a rhodium catalyst system. An increase from approximately 450 wppm iron to 1750 wppm iron results in a decrease in acetic acid STY of greater than 10%.

In view of this greater than expected significance of iron, the inventors have discovered that it is important to determine a threshold level of iron in less volatile stream 105, and thus in the reaction medium (when the process is run continuously), and to subsequently use the threshold level during the iron removal process. It should be understood that less volatile stream 111, due to the corrosion, may comprise iron in excess of the set threshold. For purposes of the present invention, the iron concentration in less volatile stream 111 would be more concentrated than the iron concentration in reaction medium due to vaporization of a portion of the reaction medium. In one embodiment, the threshold iron concentration is set at a value selected within the range from 500 wppm to 1200 wppm, e.g., 1200 wppm, 1100 wppm, 1000 wppm, 900 wppm, 800 wppm, 700 wppm, 600 wppm, or 500 wppm. When the iron in less volatile stream 111 reaches the threshold level, at least a portion of the iron is removed from the less volatile stream 111, e.g., iron is removed until the iron concentration in the less volatile stream 111 reaches a point below the threshold level. For example, if the threshold level is 1200 wppm and less volatile stream 111 comprises iron in a concentration of 1300 wppm, then at least 100 wppm iron is removed from less volatile stream 111, e.g., at least 200 wppm, at least 500 wppm, at least 1000 wppm or at least 1200 wppm. In terms of percentages of iron removed from less volatile stream 111, at least 5% of iron may be removed, e.g., at least 10%, at least 15%, at least 20%, at least 40%, at least 60% or at least 80%. To control the amount of the iron removed, the flow through slipstream 114 may be increased or decreased as needed to remove iron and achieve an iron concentration that is less than the threshold value.

Although removing all iron would be advantageous to prevent deactivation of the rhodium catalyst, the removal of iron is balanced with costs related to removing the iron as compared to the cost of replacing the rhodium catalyst that is deactivated by the iron. In some embodiments, after removing the iron through the slipstream 114, the reaction mixture may comprise iron in a concentration from 1 to 1200 wppm, e.g., from 1 to 1100 wppm, from 1 to 1000 wppm, from 10 to 1000 wppm, from 50 to 800 wppm, from 100 to 500 wppm, or from 300 to 500 wppm.

One important aspect of the aforementioned processes is the use of the threshold level of iron to determine when iron should be removed from less volatile stream 111. It is within the contemplation of the invention to employ the general principles of separation, e.g., guard bed separation, to implement the use of the threshold level of iron in this regard. The exemplary iron removal systems disclosed herein are merely exemplary and are not intended to limit the scope of the invention. Any other specific iron removal systems are within the scope of the invention, as long as the concept of the threshold level of iron is employed.

The concentration of iron in reactor 104 and/or less volatile stream 111 may be determined by off-line measurement. In some embodiments, a sample is removed from reactor 104 and/or less volatile stream 111 and analyzed by inductively coupled plasma-optical emission spectrometry. In other embodiments, a sample from reactor 104 and/or less volatile stream 111 is analyzed using inductively coupled plasma-mass spectrometry. In yet further embodiments, a sample from reactor 104 and/or less volatile stream 111 is analyzed by atomic absorption spectroscopy. In a further embodiment, there is provided a process for producing acetic acid comprising carbonylating at least one member selected from the group consisting of methanol, dimethyl ether, and methyl acetate in a reaction medium comprising water, a rhodium catalyst, methyl iodide and a halide salt, determining an iron content in a portion of the reaction medium, separating the reaction medium into a less volatile stream comprising iron and a vapor product stream, and removing at least a portion of the iron from the less volatile stream when the iron content in the reaction medium exceeds 1200 wppm.

Regardless of the method used to determine the iron concentration in reactor 104 and/or less volatile stream 111, once an iron content at or above the threshold level of iron is measured, at least a portion, e.g., a slip stream 114 of less volatile stream 111, is directed to corrosion metal removal unit 115 to form purified stream 116. Purified stream 116 has a reduced concentration of iron as compared to slip stream 114. Purified stream 116 may be combined with the remaining portion of less volatile stream 111 to form a liquid recycle 117 which is pumped into reactor 104. Corrosion metal removal unit 115 may comprise an ion exchange bed, such those disclosed in U.S. Pat. Nos. 4,894,477, 5,124,290, and 5,731,252, the entireties of which are incorporated by reference.

In one embodiment, liquid recycle 117, after removal of iron, comprises iron in an amount from 1 to 1200 wppm, e.g., from 1 to 1100 wppm, from 1 to 1000 wppm, from 10 to 1000 wppm, from 50 to 800 wppm, from 100 to 500 wppm, or from 300 to 500 wppm. The iron concentration in liquid recycle 117 generally corresponds to the iron concentration in the reaction medium in reactor 104.

The resins useful for removing iron, and potentially other corrosion metals, including nickel, chromium, and molybdenum, are cation exchange resins of the strong-acid type in their acid or lithium form. Both types are readily available as commercial products. Strong-acid cation exchange resins which are the resins preferred for use in the present invention are constituted predominantly of sulfonated styrene-divinylbenzene copolymers, although some of the available resins of this type are phenol-formaldehyde condensation polymers. Either the gel type or the macroreticular type resin is suitable but the latter is preferred, since organic components are present in the portion of the less volatile stream 111 being treated.

Contacting of the at least a portion of less volatile stream 111 and the resin can be effected in a stirred vessel wherein the resin is slurried with sufficient agitation and the less volatile stream 111 is then recovered by decantation, filtration, centrifuging, etc. However, treatment of less volatile stream 111 is usually effected by passing at least a portion of less volatile stream 111 through a fixed-bed column of the resin.

The cation exchange treatment can be effected at temperatures in the range from 0 to 120° C., although lower or higher temperatures limited only by the stability of the resin can be employed. Preferred temperatures are those in the range from 20 to 90° C. If temperatures above the boiling point of the catalyst-containing solutions are employed, then operation under pressure will be required to maintain the solution in the liquid phase. However, pressure is not a critical variable. Generally, atmospheric pressure or a pressure slightly above atmospheric is employed but superatmospheric or subatmospheric pressures can be used if desired.

The rate of flow of the slip stream through the resin during the corrosion metal removal process may be control to remove iron and may range from 1 to 20 bed volumes per hour. Preferably, lower flow rates from 1 to 12 bed volumes per hour may be employed. In addition, when the iron concentration is less than the threshold value, the flow rate of slipstream 114 may be less than 1 bed volumes per hour and may be closed until needed. After contacting, washing or rinsing of the resin bed with water or the carbonylation product from the process from which the catalyst being treated is derived such as acetic acid is essential for removing all the rhodium from the resin bed. The rinsing or washing is affected at similar flow rates as in the removal step.

In one embodiment, there is provided a process for producing acetic acid comprising carbonylating at least one member selected from the group consisting of methanol, dimethyl ether, and methyl acetate in a reaction medium comprising water in a concentration from 0.1 to 14 wt. %, a rhodium catalyst, methyl iodide and a halide salt, separating a portion of the reaction medium in a flash vessel to form a less volatile stream and a vapor product stream comprising acetic acid, recycling a liquid stream to the reactor, wherein the liquid stream comprises a portion of the less volatile stream, setting a threshold value of iron, wherein the threshold value of iron concentration is a value selected within the range from 500 wppm to 1200 wppm, determining an iron content in a portion of the reaction medium, and removing at least a portion of the iron from the liquid stream when the iron content exceeds threshold value.

In some aspects, water may be added to corrosion metal removal unit 115, or to the slip stream 114 sent to corrosion metal removal unit 115, so corrosion metal removal unit 115 comprises a water content from 0.2 to 50 wt. %, e.g., from 5 to 30 wt. % or from 5 to 15 wt. %. The addition of water to the cation exchange resin may help to improve the removal of iron and other corrosion metal products.

By removing iron from the reaction mixture until the iron content in less volatile stream 111 is less than the iron threshold level, the acetic acid STY is increased by at least 1%, e.g., by at least 5% or by at least 10%.

After the resin has become exhausted, i.e., when the corrosion metal contaminants are breaking through into the effluent, the resin can be regenerated by passing there-through a solution of alkali metals salts such as sodium, potassium or lithium salts. Generally, the lithium salt used in the regenerating cycle has a concentration in the range from 1% to 20%. Quantities employed and procedures are those well established in the art and recommended by the resin manufacturers. Aqueous lithium acetate is preferred as a regenerating agent since the acetate anion is employed in the reaction system and is readily available for use. A further advantage is that its use eliminates the rinsing step normally required after the regeneration process when other regenerates are employed.

To maximize corrosion metal regeneration capacity and to maximize resin bed column performance at relatively high concentrations of lithium acetate, the lithium acetate regeneration solution should contain some acetic acid to maintain the pH below 5.5 and avoid the formation of any insoluble corrosion metal compounds during the regeneration cycle. Precipitation of these compounds during the regeneration cycle could reduce the regeneration performance of the column and also cause plugging of the resin bed. Typically, acetic acid concentrations from 0.1 to 95 wt. % can be used, with acetic acid concentrations from 0.1 to 20 wt. % being preferred.

Recovery of Acetic Acid

The distillation and recovery of acetic acid is not particularly limited for the purposes of the present invention. In one exemplary embodiment, there is provided a process for producing acetic acid comprising separating a reaction medium formed in a reactor in a flash vessel to form a less volatile stream and a vapor product stream, distilling the vapor product stream in a first column to obtain a side stream and a low boiling overhead vapor stream comprising water in an amount of greater than or equal to 5 wt. %, condensing the low boiling overhead vapor stream and biphasically separating the condensed stream to form a heavy liquid phase and a light liquid phase, optionally treating a portion of the heavy liquid phase and/or the light liquid phase to remove at least one PRC, distilling the side stream in a second column to obtain a crude acetic acid product in the from the second column, contacting the crude acetic acid product with a metal-exchanged ion exchange resin having acid cation exchange sites to produce a purified acetic acid. The process further comprises recycling a liquid stream to the reactor, wherein the liquid stream comprises a portion of the less volatile stream and one or more recycle streams from the first and/or second columns, and removing a portion of the iron from the liquid stream to maintain an effective STY of the rhodium catalyst of at least 80% of the maximum STY. Various embodiments of primary purification train having up to 2 distillation columns is further described herein.

First Column

The overhead stream from flash vessel 110 is directed to the light ends column 120 as vapor product stream 112, where distillation yields a low-boiling overhead vapor stream 122, a sidedraw 123 that contains acetic acid, and a high boiling residue stream 121. In one embodiment, vapor product stream 112 may comprise acetic acid, methyl acetate, water, methyl iodide, and acetaldehyde, along with other impurities such as hydrogen iodide and crotonaldehyde, and byproducts such as propionic acid. Acetic acid removed via sidedraw 123 preferably is subjected to further purification, such as in drying column 125 for selective separation of acetic acid from water.

Light ends column 120 also preferably forms residuum or bottoms stream 121, which comprises primarily acetic acid and water. Although the concentration of acetic acid may be relatively high in high boiling residue stream 121, the mass flow of the high boiling residue stream 121 relative to side stream 123 is very small. In embodiments, the mass flow of the boiling residue stream 116 is no more than 0.75% of side stream 128, e.g., no more than 0.55%, or no more than 0.45%. Since light ends bottoms stream 121 typically comprises some residual catalyst, it may be beneficial to recycle all or a portion of light ends bottoms stream 121 to reactor 104. Light ends bottoms stream 121 may be combined with the less volatile stream 111 and returned together to reactor 104, as shown in FIG. 1. Due to the possibility of iron, as well as other corrosion metals, a portion of light ends bottoms stream 121 may be treated along with a portion of less volatile stream 111 to remove iron. In some embodiments, the iron in bottoms stream 121 is accumulated entrained iron from flasher vessel 110. In embodiments, light ends bottoms stream 121 may have an iron concentration that is no more than 50 wppm, e.g., no more than 45 wppm, no more than 40 wppm, no more than 35 wppm, no more than 30 wppm, no more than 25 wppm, no more than 20 wppm, no more than 15 wppm, no more than 10 wppm, or no more than 5 wppm, and/or the iron concentration in the light ends bottoms stream 121 may be greater than or equal to 0 wppm, e.g., greater than or equal to 0.1 wppm, greater than or equal to 0.5 wppm, greater than or equal to 0.75 wppm, or greater than or equal to 1 wppm.

In one embodiment, low-boiling overhead vapor stream 122 comprises water in amount greater than or equal to 5 wt. %, e.g., greater than or equal to 10 wt. %, or greater than or equal to 25 wt. %. The amount of water may be up to 80 wt. %. In terms of ranges, water concentration in the overhead may be from 5 wt. % to 80 wt. %, e.g., from 10 wt. % to 70 wt. % or from 25 wt. % to 60 wt. %. Reducing water concentration to less than 5 wt. % is not advantageous because this results in a large recycle of acetic acid back to the reaction system that sets up a large recycle through the entire purification system. In addition to water, low-boiling overhead vapor stream 122 may also comprise methyl acetate, methyl iodide, and carbonyl impurities, which are preferably concentrated in the overhead to be removed from acetic acid in side stream 123. These carbonyl impurities may also be referred to herein as PRC's.

As shown, low-boiling overhead vapor stream 122 preferably is condensed and directed to an overhead phase separation unit, as shown by overhead decanter 124. Conditions are desirably maintained such that the condensed low-boiling overhead vapor stream 122, once in decanter 124, may separate to form a light liquid phase 132 and a heavy liquid phase 133. The phase separation should be maintain two separate phase, without forming a third phase or emulsion between the phases. An offgas component may be vented via line 131 from decanter 124. In embodiments, the average residence time of the condensed low-boiling overhead vapor stream 122 in overhead decanter 124 is greater than or equal to 1 minute, e.g., greater than or equal to 3 minutes, greater than or equal to 5 minutes, or greater than or equal to 10 minutes, and/or the average residence time is no more than 60 minutes, e.g., no more than 45 minutes, or no more than 30 minutes, or no more than 25 minutes.

Although the specific compositions of the light phase stream 132 may vary widely, some preferred compositions are provided below in Table 1.

TABLE 1

Exemplary Light Liquid Phase from Light Ends Overhead

|  | conc. (Wt. %) | conc. (Wt. %) | conc. (Wt. %) |
|---|---|---|---|
| HOAc | 1-40 | 1-25 | 5-15 |
| Water | 50-90 | 50-80 | 60-80 |
| PRC's | <5 | <3 | <1 |
| MeI | <10 | <5 | <3 |
| MeAc | 1-50 | 1-25 | 1-15 |

In one embodiment, overhead decanter 124 is arranged and constructed to maintain a low interface level to prevent an excess hold up of methyl iodide. Although the specific compositions of heavy liquid phase 133 may vary widely, some exemplary compositions are provided below in Table 2.

TABLE 2

Exemplary Heavy Liquid Phase from Light Ends Overhead

|  | conc. (Wt. %) | conc. (Wt. %) | conc. (Wt. %) |
|---|---|---|---|
| Water | 0.01-2 | 0.05-1 | 0.1-0.9 |
| Methyl Acetate | 0.1-25 | 0.5-20 | 0.7-15 |
| Acetic Acid | 0.1-10 | 0.2-8 | 0.5-6 |
| PRC's | <5 | <3 | <1 |
| Methyl Iodide | 40-98 | 50-95 | 60-85 |

The density of the heavy liquid phase 133 may be from 1.3 to 2, e.g., from 1.5 to 1.8, from 1.5 to 1.75 or from 1.55 to 1.7. As described in U.S. Pat. No. 6,677,480, the measured density in the heavy liquid phase 133 correlates with the methyl acetate concentration in the reaction medium. As density decreases, the methyl acetate concentration in the reaction medium increases. In one embodiment of the present invention, heavy liquid phase 133 is recycled to the reactor and the light liquid phase 132 is controlled to be recycled through the same pump. It may be desirable to recycle a portion of the light liquid phase 132 that does not disrupt the pump and maintains a density of the combined light liquid phase 132 and heavy liquid phase 133 of greater than or equal to 1.3, e.g., greater than or equal to 1.4, greater than or equal to 1.5, or greater than or equal to 1.7. As described herein, a portion of the heavy liquid phase 133 may be treated to remove impurities such as acetaldehyde.

As shown in FIG. 1, the light phase exits decanter 124 via stream 132. A first portion, e.g., aliquot portion, of light phase stream 132 is recycled to the top of the light ends column 120 as reflux stream 134. In other embodiments a portion of the heavy liquid phase 133 may also be refluxed (not shown) to the light ends column 120. A portion of light phase stream 132 may be recycled to reactor 104 by stream 135. In one embodiment, stream 135 and/or heavy liquid phase 133, may comprise corrosion metals, including iron, nickel, chromium, and/or molybdenum. Heavy liquid phase 133 may be fed directly to reactor 104. Stream 135 may be combined with stream 137 to form stream 138 and a portion of this stream is mixed with a slipstream 114 of less volatile stream 111. The remaining portion of stream 138, shown by stream 138' may be combined with liquid recycle 117. This allows adjustment of the aqueous amount in slipstream 114. In embodiments, stream 135 and/or heavy liquid phase 133 may have an iron concentration that is no more than 5 wppm, e.g., no more than 2.5 wppm, no more than 1.2 wppm, no more than 1 wppm, no more than 0.5 wppm, or no more than 0.1 wppm, no more thanno more thanno more thanno more than and/or the iron concentration in stream 135 and/or heavy liquid phase 133 may be greater than or equal to 0 wppm, e.g., greater than or equal to 0.01 wppm, greater than or equal to 0.05 wppm, greater than or equal to 0.1 wppm, greater than or equal to 0.25 wppm, or greater than or equal to 0.5 wppm.

PRC Removal System

As described herein the light ends column 120 is part of the primary purification train. In some embodiments, a portion of light liquid phase and/or heavy liquid phase may be separated and directed to acetaldehyde or PRC removal system (not shown) to recover methyl iodide and methyl acetate, while removing acetaldehyde. For purposes of the present invention, the acetaldehyde or PRC removal system is not part of the primary purification train. In some embodiments, it may be desirous to use an acetaldehyde or PRC removal system to reduce the acetaldehyde concentration in the reaction medium. The acetaldehyde or PRC removal system produces a stream enriched in acetaldehyde that may be purged or otherwise not returned to the reactor. As described herein, the reaction medium preferably comprises acetaldehyde in an amount of no more than 1500 wppm.

As shown in Tables 1 and 2, light liquid phase 132 and/or heavy liquid phase 133 each contain PRC's and the process may include removing carbonyl impurities, such as acetaldehyde, that deteriorate the quality of the acetic acid product and may be removed in suitable impurity removal columns and absorbers as described in U.S. Pat. Nos. 6,143,930; 6,339,171; 7,223,883; 7,223,886; 7,855,306; 7,884,237; 8,889,904; and US Pub. Nos. 2006/0011462, which are incorporated herein by reference in their entirety. Carbonyl impurities, such as acetaldehyde, may react with iodide catalyst promoters to form alkyl iodides, e.g., ethyl iodide, propyl iodide, butyl iodide, pentyl iodide, hexyl iodide, etc. Also, because many impurities originate with acetaldehyde, it is desirable to remove carbonyl impurities from the liquid light phase.

The portion of light liquid phase 132 and/or heavy liquid phase 133 fed to the acetaldehyde or PRC removal system may vary from 1% to 99% of the mass flow of either the light liquid phase 138 and/or heavy liquid phase 118, e.g., from 1 to 50%, from 2 to 45%, from 5 to 40%, 5 to 30% or 5 to 20%. Also in some embodiments, a portion of both the light liquid phase 132 and heavy liquid phase 133 may be fed to the acetaldehyde or PRC removal system. The portion of the light liquid phase 132 not fed to the acetaldehyde or PRC removal system may be refluxed to the first column or recycled to the reactor, as described herein. The portion of the heavy liquid phase 133 not fed to the acetaldehyde or PRC removal system may be recycled to the reactor. Although a portion of heavy liquid phase 133 may be refluxed to the light ends column, it is more desirable to return the methyl iodide enriched heavy liquid phase 133 to the reactor.

In one embodiment, a portion of light liquid phase 132 and/or heavy liquid phase 133 is fed to a distillation column which enriches the overhead thereof to have acetaldehyde and methyl iodide. Depending on the configuration, there may be two separate distillation columns, and the overhead of the second column may be enriched in acetaldehyde and methyl iodide. Dimethyl ether, which may be formed in-situ, may also be present in the overhead. The overhead may be subject to one or more extraction stages to remove a raffinate enriched in methyl iodide and an extractant. A portion of the raffinate may be returned to the distillation column, first column, overhead decanter and/or reactor. For example, when the heavy liquid phase 133 is treated in the PRC removal system, it may be desirable to return a portion the raffinate to either the distillation column or reactor. Also, for example, when light liquid phase 132 is treated in the PRC removal system, it may be desirable to return a portion the raffinate to either the first column, overhead decanter, or reactor. In some embodiments, the extractant may be further distilled to remove water, which is returned to the one or more extraction stages. The column bottoms, which contains more methyl acetate and methyl iodide than light liquid phase 132, may also be recycled to reactor 104 and/or refluxed to light ends column 120.

Second Column

Acetic acid removed via side stream 123 preferably is subjected to further purification, such as in a second column 125, also referred to as a drying column, and separates side stream 123 to form aqueous overhead stream 126 comprised primarily of water and product stream 127 comprised primarily of acetic acid. Water from the side stream is concentrated in the aqueous overhead stream and the aqueous overhead comprises greater than or equal to 90% of the water in the side stream fed to the second column, e.g., greater than or equal to 95%, greater than or equal to 97%, greater than or equal to 99%. Aqueous overhead stream 126 may comprise water in an amount from 50 to 75 wt. %. In embodiments, aqueous overhead stream may comprise water in an amount of no more than 75 wt. %, e.g., no more than 70 wt. %, no more than 65 wt. %. Methyl acetate and methyl iodide are also removed from the side stream and concentrated in the overhead stream. Product stream 127 preferably comprises or consists essentially of acetic acid and may be withdrawn in the bottom of second column 125 or a side stream near the bottom. When withdrawn as a side stream near the bottom, the side stream may be a liquid or a vapor stream. In preferred embodiments, product stream 127 comprises acetic acid in an amount greater than or equal to 90 wt. %, e.g., greater than or equal to 95 wt. % or greater than or equal to 98 wt. %. Product stream 127 may be further processed, e.g., by passing through an ion exchange resin, prior to being stored or transported for commercial use.

Similarly, aqueous overhead stream 126 from second column 125 contains a reaction component, such as methyl iodide, methyl acetate, and water, and it is preferable to retain these reaction components within the process. Aqueous overhead stream 126 is condensed by a heat exchanger into stream 137, which is recycled to reactor 104 and/or refluxed second column 125. An offgas component may be vented via line 136 from condensed low-boiling overhead vapor stream 126. Similar to the condensed low-boiling overhead vapor stream from first column 120, condensed overhead stream 137 may also be separated to form an aqueous phase and an organic phase, and these phases may be recycled or refluxed as needed to maintain the concentrations in the reaction medium. In one embodiment, condensed overhead stream 137 may be combined with stream 135 to form stream 138. A portion of stream 138 is mixed with slipstream 114 and treated to remove iron in corrosion metal removal unit 115. In embodiments, condensed overhead stream 137 may have an iron concentration that is no more than 5 wppm, e.g., no more than 2.5 wppm, no more than 1.2 wppm, no more than 1 wppm, no more than 0.9 wppm, no more than 0.75 wppm, no more than 0.5 wppm, or no more than 0.1 wppm, no more thanno more than and/or the iron concentration in the condensed overhead stream 137 may be greater than or equal to 0 wppm, e.g., greater than or equal to 0.01 wppm, greater than or equal to 0.05 wppm, greater than or equal to 0.1 wppm, greater than or equal to 0.2 wppm, or greater than or equal to 0.3 wppm.

In one embodiment, the side stream water concentration is controlled to balance the water in both the first and second columns. When water in an amount no more than 14 wt. % is used in the reaction medium, more preferably, no more than 4.1 wt. %, there may not be sufficient water in the second column to stably operate the column. Although it may be possible to reduce the water concentration in the side stream to no more than 1 wt. %, this would result in an imbalance in the second column, which may cause the recovery of acetic acid to become more difficult and result in off-spec product. Further, by having water in the side stream the second column is able to remove that water in the aqueous overhead. The recycle ratio between the light liquid phase from the first column and the aqueous overhead from the second column helps to maintain desirable water concentrations in the reactor while maintaining stable operations in the first and second distillation columns. In one embodiment, the recycle ratio of the mass flow of the light liquid phase recycled to the reactor to the mass flow of the aqueous overhead to the reactor is no more than 2, e.g., no more than 1.8, no more than 1.5, no more than 1, no more than 0.7, no more than 0.5, no more than 0.35, no more than 0.25 and/or the recycle ratio of the mass flow of the light liquid phase recycled to the reactor to the mass flow of the aqueous overhead to the reactor is greater than or equal to 0, e.g., greater than or equal to 0.05, greater than or equal to 0.1, greater than or equal to 0.15, or greater than or equal to 0.2. In one embodiment, the recycle ratio of the mass flow of the light liquid phase recycled to the reactor to the mass flow of the aqueous overhead to the reactor is from 0 to 2, e.g., from 0 to 1.5, from 0 to 1.3, from 0 to 1, from 0 to 0.9 from 0 to 0.7, from 0 to 0.5, from 0 to 0.35 or from 0 to 0.25.

To recover residue liquids from the vent streams, in particular lines 106, 131, and 136, these lines may be fed to a scrubber that operates with chilled methanol and/or acetic acid to remove methyl acetate and methyl iodide. A suitable scrubber is described in U.S. Pat. No. 8,318,977, which is incorporated herein by reference in its entirety.

The distillation columns of the present invention may be a conventional distillation column, e.g., a plate column, a packed column, and others. Plate columns may include a perforated plate column, bubble-cap column, Kittel tray column, uniflux tray, or a ripple tray column. For a plate column, the theoretical number of plates is not particularly limited. Depending on the species of the component to be separate, the plate column may include up to 80 plates, e.g., from 2 to 80, from 5 to 60, from 5 to 50, or more preferably from 7 to 35. The distillation column may include a combination of different distillation apparatuses. For example, a combination of bubble-cap column and perforated plate column may be used as well as a combination of perforated plate column and a packed column.

The distillation temperature and pressure in the distillation system can suitably be selected depending on the condition such as the species of the objective carboxylic acid and the species of the distillation column, or the removal target selected from the lower boiling point impurity and the higher boiling point impurity according to the composition of the feed stream. For example, in a case where the purification of acetic acid is carried out by the distillation column, the inner pressure of the distillation column (usually, the pressure of the column top) may be from 0.01 to 1 MPa, e.g., from 0.02 to 0.7 MPa, and more preferably from 0.05 to 0.5 MPa in terms of gauge pressure. Moreover, the distillation temperature for the distillation column, namely the inner temperature of the column at the temperature of the column top, can be controlled by adjusting the inner pressure of the column, and, for example, may be from 20 to 200° C., e.g., from 50 to 180° C., and more preferably 100 to 160° C.

The material of each member or unit associated with the distillation system, including the columns, valves, condensers, receivers, pumps, reboilers, and internals, and various lines, each communicating to the distillation system may be suitable material such as glass, metal, ceramic, or combinations thereof, and is not particularly limited to a specific one. According to the present invention, the material of the foregoing distillation system and various lines are a transition metal or a transition-metal-based alloy such as iron alloy, e.g., a stainless steel, nickel or nickel alloy, zirconium or zirconium alloy thereof, titanium or titanium alloy thereof, or aluminum alloy. Suitable iron-based alloys include those containing iron as a main component, e.g., a stainless steel that also comprises chromium, nickel, molybdenum and others. Suitable alloys include those containing nickel as a main component and one or more of chromium, iron, cobalt, molybdenum, tungsten, manganese, and others, e.g., HASTELLOY™ and INCONEL™ Corrosion-resistant metals may be particularly suitable as materials for the distillation system and various lines.

Guard Bed

Carboxylic acid streams, e.g., acetic acid streams, that are contaminated with a halides and/or corrosion metals may be contacted with an ion exchange resin composition under a wide range of operating conditions. Preferably, the ion exchange resin composition is provided in a guard bed. The use of guard beds to purify contaminated carboxylic acid streams is well documented in the art, for example, U.S. Pat. Nos. 4,615,806; 5,653,853; 5,731,252; and 6,225,498, which are hereby incorporated by reference in their entireties. Generally, a contaminated liquid carboxylic acid stream is contacted with an ion exchange resin composition, which is preferably disposed in the guard bed. The halide contaminants, e.g., iodide contaminants, react with the metal to form metal iodides. In some embodiments, hydrocarbon moieties, e.g., methyl groups, that may be associated with the iodide may esterify the carboxylic acid. For example, in the case of acetic acid contaminated with methyl iodide, methyl acetate would be produced as a byproduct of the iodide removal. The formation of this esterification product typically does not have a deleterious effect on the treated carboxylic acid stream.

In one embodiment, the ion exchange resin is a metal-exchanged ion exchange resin and may comprise at least one metal selected from the group consisting of silver, mercury, palladium and rhodium. In one embodiment, at least 1% of the strong acid exchange sites of said metal-exchanged resin are occupied by silver. In another embodiment, at least 1% of the strong acid exchange sites of said metal-exchanged resin are occupied by mercury. The process may further comprise treating the purified acetic acid product with a cationic exchange resin to recover any silver, mercury, palladium or rhodium.

The pressure during the contacting step is limited only by the physical strength of the resin. In one embodiment, the contacting is conducted at pressures ranging from 0.1 MPa to 1 MPa, e.g., from 0.1 MPa to 0.8 MPa or from 0.1 MPa to 0.5 MPa. For convenience, however, both pressure and temperature preferably may be established so that the contaminated carboxylic acid stream is processed as a liquid. Thus, for example, when operating at atmospheric pressure, which is generally preferred based on economic considerations, the temperature may range from 17° C. (the freezing point of acetic acid) to 118° C. (the boiling point of acetic acid). It is within the purview of those skilled in the art to determine analogous ranges for product streams comprising other carboxylic acid compounds. The temperature of the contacting step preferably is kept relatively low to minimize resin degradation. In one embodiment, the contacting is conducted at a temperature ranging from 25° C. to 120° C., e.g., from 25° C. to 100° C. or from 50° C. to 100° C. Some cationic macroreticular resins typically begin degrading (via the mechanism of acid-catalyzed aromatic desulfonation) at temperatures of 150° C. Carboxylic acids having up to 5 carbon atoms, e.g., up to 3 carbon atoms, remain liquid at these temperatures. Thus, the temperature during the contacting should be maintained below the degradation temperature of the resin utilized. In some embodiments, the operating temperature is kept below temperature limit of the resin, consistent with liquid phase operation and the desired kinetics for halide removal.

The configuration of the guard bed within an acetic acid purification train may vary widely. For example, the guard bed may be configured after a drying column. Additionally or alternatively, the guard bed may be configured after a heavy ends removal column or finishing column. Preferably the guard bed is configured in a position wherein the temperature acetic acid product stream is low, e.g., no more than 120° C. or no more than 100° C. Aside from the advantages discussed above, lower temperature operation provides for less corrosion as compared to higher temperature operation. Lower temperature operation provides for less formation of corrosion metal contaminants, which, as discussed above, may decrease overall resin life. Also, because lower operating temperatures result in less corrosion, vessels advantageously need not be made from expensive corrosion-resistant metals, and lower grade metals, e.g., standard stainless steel, may be used.

In one embodiment, the flow rate through the guard bed ranges from 0.1 bed volumes per hour ("BV/hr") to 50 BV/hr, e.g., 1 BV/hr to 20 BV/hr or from 6 BV/hr to 10 BV/hr. A bed volume of organic medium is a volume of the medium equal to the volume occupied by the resin bed. A flow rate of 1 BV/hr means that a quantity of organic liquid equal to the volume occupied by the resin bed passes through the resin bed in a one hour time period.

To avoid exhausting the resin with a purified acetic acid product that is high in total iodide concentration, in one embodiment the purified acetic acid product in bottoms stream 127 is contacted with a guard bed when total iodide concentration of the purified acetic acid product is no more than 5 wppm, e.g., preferably no more than 1 wppm. Total iodide concentration includes iodide from both organic, $C_1$ to $C_{14}$ alkyl iodides, and inorganic sources, such as hydrogen iodide. A purified acetic acid composition is obtained as a result of the guard bed treatment. The purified acetic acid composition, in one embodiment, comprises iodides in a total concentration of no more than 100 wppb, e.g., no more than 90 wppb, no more than 50 wppb, or no more than 25 wppb. In one embodiment, the purified acetic acid composition comprises no more than 1000 wppb corrosion metals, e.g., no more than 750 wppb, no more than 500 wppb, or no more than 250 wppb. For purposes of the present invention, corrosion metals include metals selected from the group consisting of nickel, iron, chromium, molybdenum and combinations thereof. In terms of ranges, the purified acetic acid composition may comprise from 0 to 100 wppb iodides, e.g., from 1 to 50 wppb, and/or from 0 to 1000 wppb corrosion metals, e.g., from 1 to 500 wppb. In other embodiments, the guard bed removes at least 25 wt. % of the iodides from the crude acetic acid product, e.g., at least 50 wt. % or at least 75 wt. %. In one embodiment, the guard bed removes at least 25 wt. % of the corrosion metals from the crude acetic acid product, e.g., at least 50 wt. % or at least 75 wt. %.

In another embodiment, the product stream may be contacted with cationic exchanger to remove lithium compounds. The cationic exchanger in the acid form comprises a resin of acid-form strong acid cation exchange macroreticular, macroporous or mesoporous resins. Without being bound by theory feeding a product stream to an ion-exchange comprises lithium compounds in an amount of greater than or equal to 10 wppm results in displacement of metals in the treated product. Advantageously, this may be overcome by using an cationic exchanger upstream of the ion-exchange resin. After contacting with the cationic exchanger, the product stream may have a lithium ion concentration of no more than 50 weight part per billion (wppb), e.g., no more than 10 wppb, or no more than 5 wppb.

Although the product stream may be contacted with an ion-exchange resin to remove iodides, it is preferred not to flash the product stream or contact with product stream with an adsorption system that contains activated carbon. Flashing the product stream is not efficient because there is not a sufficient pressure drop to recover greater than 50% of the acetic acid from the product stream. Thus, in one embodiment, a non-flashed portion of the product stream is fed to the ion-exchange bed to remove iodides.

As is evident from the figures and text presented above, a variety of embodiments are contemplated.

E1. A process for producing acetic acid comprising:
carbonylating at least one member selected from the group consisting of methanol, dimethyl ether, and methyl acetate in a reactor in a reaction medium comprising water, a rhodium catalyst, methyl iodide and a halide salt, wherein the rhodium catalyst is present in the reaction medium in an amount from 200 to 3000 wppm as rhodium;
separating a portion of the reaction medium in a flash vessel to form a less volatile stream and a vapor product stream comprising acetic acid;
recycling a liquid stream to the reactor, wherein the liquid stream comprises a portion of the less volatile stream and wherein the liquid stream comprises iron; and
removing a portion of the iron from the liquid stream to maintain an effective STY of the rhodium catalyst of at least 80% of the maximum STY.

E2. The process of embodiment E1, wherein the liquid stream, after removal of iron, comprises iron in an amount from 1 to 1200 wppm.

E3. The process of anyone of embodiments E1 or E2, wherein at least 5% of the iron is removed from the liquid recycle.

E4. The process of anyone of embodiments E1-E3, further comprising maintaining an iron concentration in the reaction medium of no more than 1200 wppm.

E5. The process of anyone of embodiments E1-E4, further comprising maintaining an iron concentration in the reaction medium from 100 to 500 wppm.

E6. The process of anyone of embodiments E1-E5, wherein the iron concentration in wppm is maintained to be less than the concentration of the rhodium catalyst in wppm.

E7. The process of anyone of embodiments E1-E6, wherein the effective STY of the rhodium catalyst is maintained at least 90% of the maximum STY.

E8. The process of anyone of embodiments E1-E7, further maintaining at least 85% of the rhodium needed for the effective STY to achieve 100% of the maximum STY.

E9. The process of anyone of embodiments E1-E8, wherein the less volatile stream comprises acetic acid in an amount from 60 to 90 wt. %, rhodium catalyst in an amount from 0.01 to 0.5 wt. % as rhodium, corrosion metals in a total amount from 10 to 2500 wppm, lithium iodide in an amount from 5 to 20 wt. %, methyl iodide in an amount from 1 to 25 wt. %, methyl acetate in an amount from 0.1 to 5 wt. %, and water in an amount from 0.1 to 8 wt. %.

E10. The process of anyone of embodiments E1-E9, wherein the material of the reactor comprises a transition metal or transition-metal-based alloy.

E11. The process of anyone of embodiments E1-E10, wherein the material of the flash vessel comprises a transition metal or transition-metal-based alloy.

E12. The process of anyone of embodiments E1-E11, further comprising separating the vapor product stream comprising acetic acid in a primary purification train to obtain an acetic acid product and one or more recycle streams.

E13. The process of embodiment E12, wherein the liquid stream comprises a portion of the one or more recycle streams.

E14. The process of embodiment E12, wherein at least one of the one or more recycle streams comprises iron.

E15. The process of anyone of embodiments E1-E14, further comprising directing at least one stream to a permanganate reducing compound removal system to obtain a stream enriched in acetaldehyde.

E16. The process of anyone of embodiments E1-E15, wherein the reaction medium comprises acetaldehyde in an amount of no more than 1500 wppm.

E17. The process of anyone of embodiments E1-E16, wherein iron is removed from the liquid stream by contacting a portion of the liquid stream with a cation exchange resin.

E18. A process for producing acetic acid comprising:
carbonylating at least one member selected from the group consisting of methanol, dimethyl ether, and methyl acetate in a reactor in a reaction medium comprising a rhodium catalyst, methyl iodide and a halide salt, wherein the rhodium catalyst is present in the reaction medium in an amount from 200 to 3000 wppm as rhodium;
separating a portion of the reaction medium in a flash vessel to form a less volatile stream and a vapor product stream comprising acetic acid;
recycling a liquid stream to the reactor, wherein the liquid stream comprises a portion of the less volatile stream and wherein the liquid stream comprises iron; and
removing a portion of the iron from the liquid stream to maintain an iron concentration in the reaction medium of no more than 1200 wppm.

E19. The process of embodiments E18, further comprising maintaining an iron concentration in the reaction medium from 100 to 500 wppm.

E20. The process of anyone of embodiments E18 or E19, wherein the iron concentration in wppm is maintained to be less than the concentration of the rhodium catalyst in wppm.

E21. The process of anyone of embodiments E18-E20, wherein the reaction medium comprises acetaldehyde in an amount of no more than 1500 wppm.

E22. The process of anyone of embodiments E18-E21, wherein the less volatile stream comprises acetic acid in an amount from 60 to 90 wt. %, rhodium catalyst in an amount from 0.01 to 0.5 wt. % as rhodium, corrosion metals in a total amount from 10 to 2500 wppm, lithium iodide in an amount from 5 to 20 wt. %, methyl iodide in an amount from 1 to 25 wt. %, methyl acetate in an amount from 0.1 to 5 wt. %, and water in an amount from 0.1 to 8 wt. %.

E23. A process for producing acetic acid comprising:
carbonylating at least one member selected from the group consisting of methanol, dimethyl ether, and methyl acetate in a reaction medium comprising water, a rhodium catalyst, methyl iodide and a halide salt, wherein the reaction medium comprises water in an amount from 0.1 to 14 wt. %;
separating a portion of the reaction medium in a flash vessel to form a less volatile stream and a vapor product stream comprising acetic acid;
recycling a liquid stream to the reactor, wherein the liquid stream comprises a portion of the less volatile stream;
setting a threshold value of iron for the portion of the reaction medium, wherein the threshold value of iron concentration is a value selected within the range from 500 wppm to 1200 wppm;
determining an iron content in the portion of the reaction medium; and
removing at least a portion of the iron from the liquid stream when the iron content exceeds threshold value.

E24. The process of embodiment E23, wherein the reaction medium comprises acetaldehyde in an amount of no more than 1500 wppm.

E25. The process of anyone of embodiments E23 or E24, wherein the less volatile stream comprises acetic acid in an amount from 60 to 90 wt. %, rhodium catalyst in an amount from 0.01 to 0.5 wt. % as rhodium, corrosion metals in a total amount from 10 to 2500 wppm, lithium iodide in an amount from 5 to 20 wt. %, methyl iodide in an amount from 1 to 25 wt. %, methyl acetate in an amount from 0.1 to 5 wt. %, and water in an amount from 0.1 to 8 wt. %.

E26. The process of anyone of embodiments E23-E25, further comprising separating the vapor product stream comprising acetic acid in a primary purification train to obtain an acetic acid product and one or more recycle streams.

E27. The process of anyone of embodiments E23-E26, wherein the liquid stream comprises a portion of the one or more recycle streams.

E28. The process of anyone of embodiments E23-E27, further comprising determining an iron content in the portion of the one or more recycle streams, and removing at least a portion of the iron from the portion of the one or more recycle streams when the iron content exceeds the threshold value.

E29. A process for producing acetic acid comprising:
carbonylating at least one member selected from the group consisting of methanol, dimethyl ether, and methyl acetate in a reaction medium comprising water, a rhodium catalyst, methyl iodide and a halide salt, wherein the reaction medium comprises from 0.1 to 14 wt. % water;
determining an iron content in the reaction medium;
separating the reaction medium into a less volatile stream comprising iron and a vapor product stream; and
removing at least a portion of the iron from the less volatile stream when the iron content in the reaction medium exceeds 1200 wppm.

E30. The process of embodiment E29, wherein at least 5% of the iron is removed from the less volatile stream.

E31. The process of anyone of embodiments E29 or E30, wherein the removing also comprises removing corrosion metal contaminants other than iron.

E32. The process of anyone of embodiments E29-E31, wherein the corrosion metal contaminants other than iron are selected from the group consisting of nickel, chromium, molybdenum and combinations thereof.

E33. The process of anyone of embodiments E29-E32, wherein the removing iron comprises: contacting the less volatile stream with an ion exchange resin and water in an amount sufficient to bring the water concentration of the liquid recycle as it proceeds through the contacting cycle within a range of 0.25 wt. % to 50 wt. % and, recover a purified liquid recycle solution comprising less than 1200 ppm iron.

E34. The process of embodiment E33, wherein the resin is a strong-acid cation exchange resin.

E35. The process of embodiment E33, wherein the contacting is effected by passing the less volatile stream through a fixed-bed column of said resin.

E36. The process of embodiment E33, wherein said resin is regenerated after exhaustion by washing with an alkali metal salt.

E37. The process of embodiment E36, wherein the alkali metal salt is lithium acetate.

E38. The process of embodiment E36, wherein the alkali metal is potassium.

E39. The process of embodiment E36, wherein the alkali metal is sodium.

E40. The process of embodiment E33, wherein the water concentration of the less volatile stream as it proceeds through the contacting cycle is within a range of 5 wt. % to 30 wt. %.

E41. The process of anyone of embodiments E29-E40, wherein at least a portion of the less volatile stream is returned to the reactor.

E42. A process for improving the productivity of a less volatile stream comprising a set water and alkali metal ion concentration and greater than 1200 ppm iron, wherein the process comprises contacting the less volatile stream in a contacting cycle with a cation exchange resin and water in an amount sufficient to bring the water concentration of the less volatile stream as it proceeds through the contacting cycle within a range of 0.25 to 50 wt. %.

E43. The process of embodiment E42, wherein the productivity is improved by at least 10%.

E44. The process of anyone of embodiments E42 or E43, wherein the water concentration of the less volatile stream as it proceeds through the contacting cycle is within a range of 5 to 30 wt. %.

E45. The process of embodiment E44, wherein the water concentration of the less volatile stream as it proceeds through the contacting cycle is within a range of 5 to 15 wt. %.

E46. A process for improving the productivity of a less volatile stream employed under low water conditions, said solution containing rhodium and alkali metal and further containing greater than 1200 ppm iron, wherein the process comprises contacting the less volatile stream with an ion exchange resin and water in an amount sufficient to bring the water concentration of the less volatile stream as it proceeds through the contacting cycle within a range of 0.25 to 50 wt. % and, recover a stream comprising less than 1200 ppm iron.

E47. The process of embodiment E46, wherein the water concentration of the less volatile stream as it proceeds through the contacting cycle is within a range of 5 to 30 wt. %.

E48. The process of anyone of embodiments E46 or E47, wherein the water concentration of the less volatile stream as it proceeds through the contacting cycle is within a range of 5 to 15 wt. %.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

EXAMPLES

The present invention will be better understood in view of the following non-limiting examples.

Example 1

A portion of a reaction medium formed according to the process described herein comprised from 8 to 10 wt. % lithium iodide, from 3 to 6 wt. % water, from 2.2 to 3.3 wt. % methyl acetate and from 10.7 to 12.5 wt. % methyl iodide. The portion of the reaction medium was measured at several different times for the corrosion metal content, the methane space time yield change (%; methane inefficiency), the carbon dioxide space time yield change (%; carbon dioxide inefficiency) and the acetic acid space time yield. The results are shown in Table 3.

TABLE 3

Corrosion Metal Content and Effect on Space Time Yield

| Sample | Ni (ppm) | Mo (ppm) | Fe (ppm) | Cr (ppm) | Total Corrosion Metals (ppm) | CH4 STY (%) | CO2 STY (%) | HOAc STY (mol/L · hr) |
|---|---|---|---|---|---|---|---|---|
| A | 1750 | 620 | 2690 | 250 | 5310 | 0.91 | 0.81 | 7.7 |
| B | 1170 | 450 | 1750 | 200 | 3570 | 0.54 | 0.40 | 9.1 |
| C | 237 | 80 | 29 | 18 | 364 | 0.08 | 0.20 | 11.3 |
| D | 2469 | 931 | 372 | 460 | 4232 | 0.38 | 0.25 | 10.5 |
| E | 1962 | 842 | 1889 | 714 | 5523 | 0.70 | 0.60 | 9.0 |
| F | 1767 | 755 | 1300 | 517 | 4339 | 0.70 | 0.60 | 8.3 |
| G | 1932 | 717 | 1444 | 525 | 4678 | 0.90 | 0.60 | 7.5 |
| H | 1187 | 515 | 743 | 303 | 2748 | 0.40 | 0.30 | 7.6 |
| I | 1473 | 605 | 738 | 341 | 3157 | 0.40 | 0.20 | 8.7 |

Figure 4:
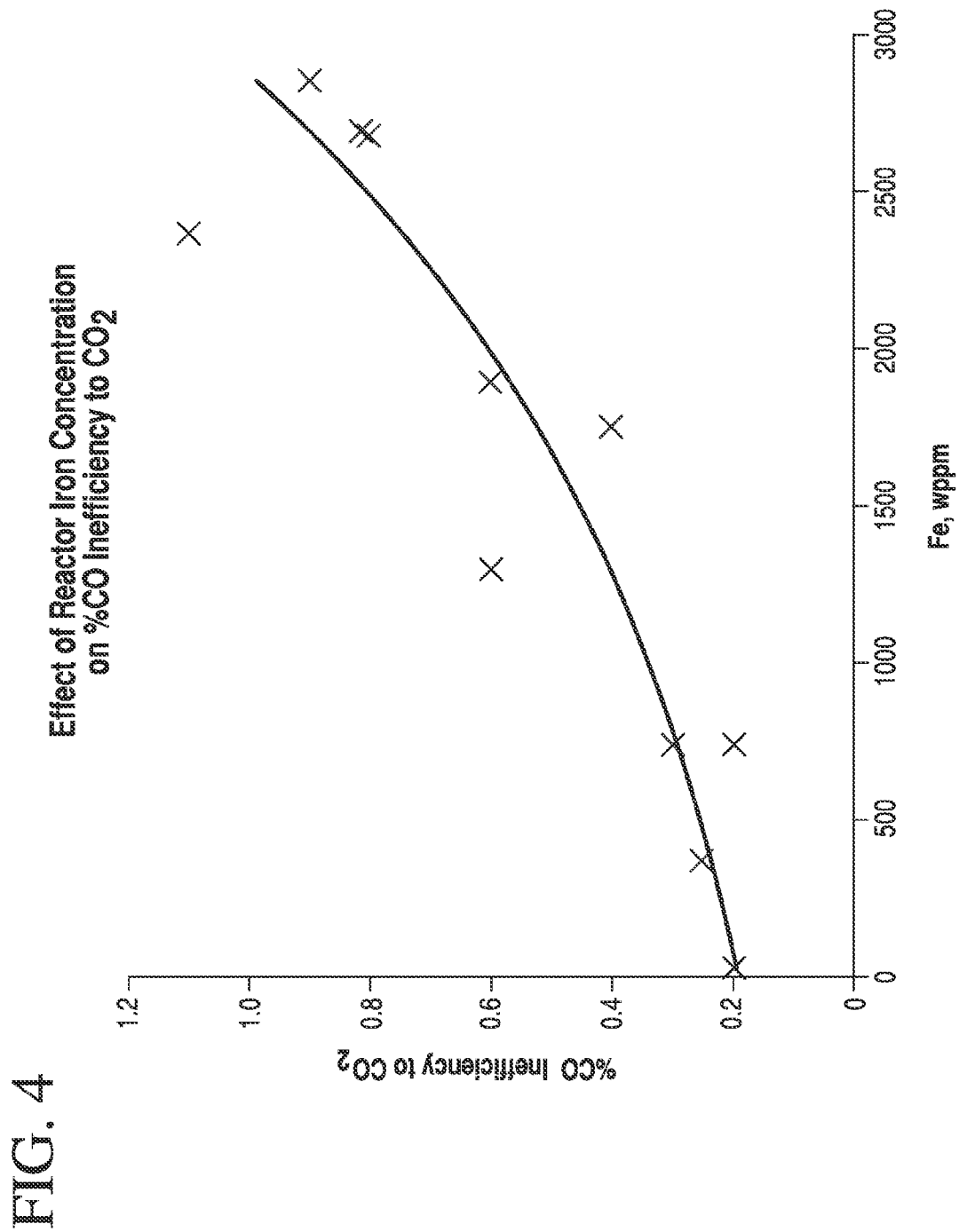
FIG. 4 illustrates the effect of iron concentration on carbon dioxide inefficiency.
Figure 5:
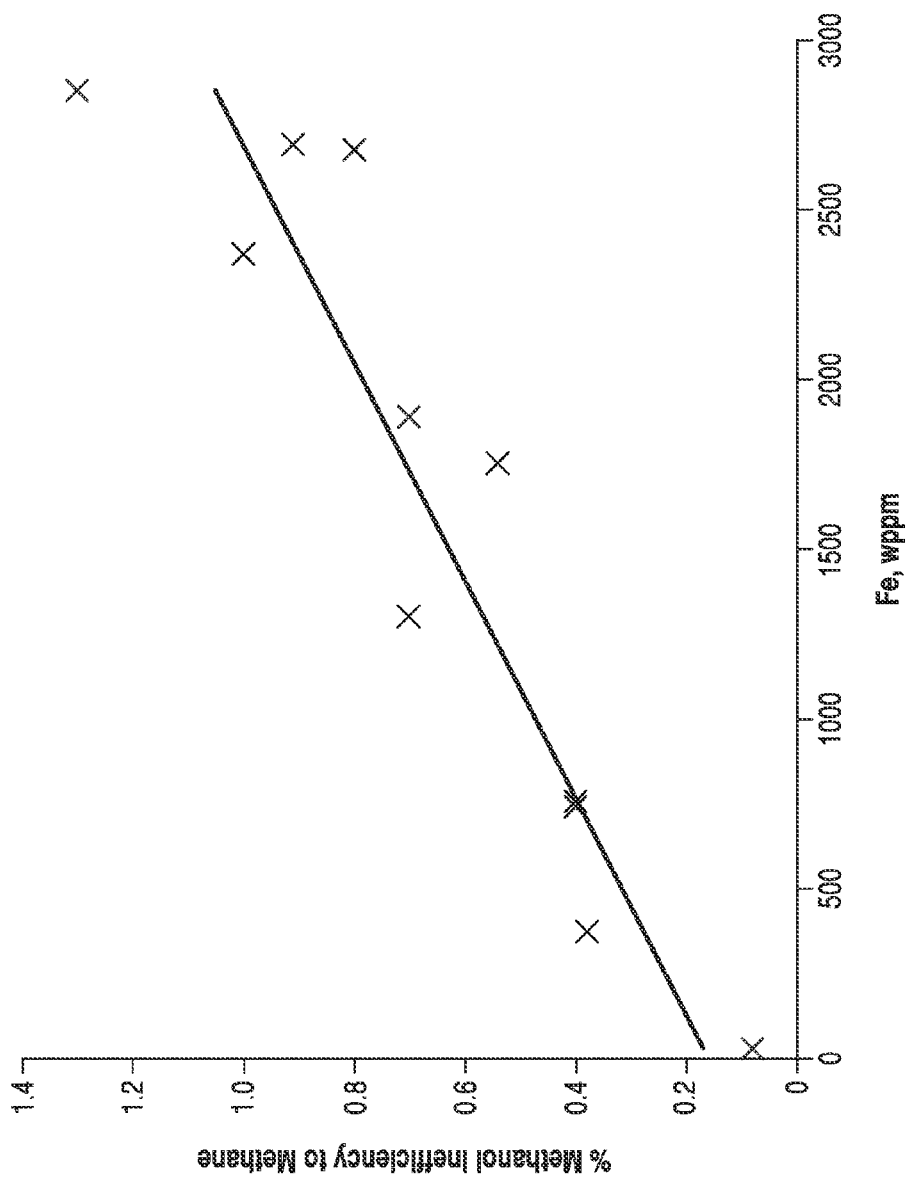
FIG. 5 illustrates the effect of iron concentration on methane inefficiency.

As shown in Table 3, as corrosion metals increases, the percent inefficiency of $CH_4$ and $CO_2$ are also increased. Case D and E shows that the iron has most effect while case C and D and case E and F show Ni also has negative effect, but such effect is less severe than Fe. Cases E, F, and G show that the trend of inefficiency does not follow the changes of Chromium. This data is also shown graphically in FIGS. 4 and 5.

Example 2

Figure 6:
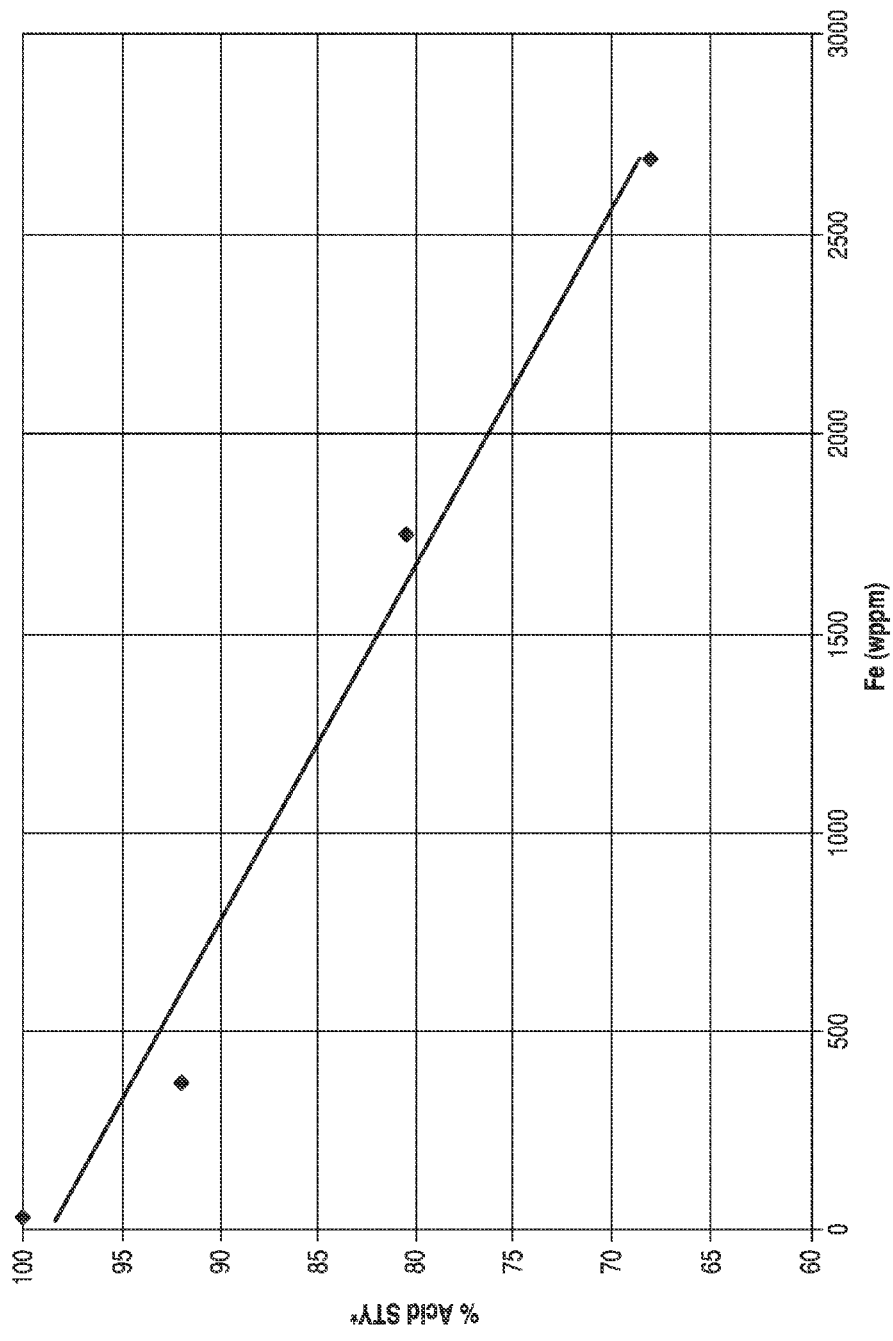
FIG. 6 illustrates the percent change in space time yield for acetic acid versus iron concentration.

A portion of a reaction medium formed according to the process described herein comprised from 15 to 18 wt. % lithium iodide, from 2.5 to 3.5 wt. % water, from 3.0 to 4.0 wt. % methyl acetate and from 11.0 to 14.0 wt. % methyl iodide and from 450 to 650 wppm rhodium was measured off-line at four discrete iron concentrations. As shown in FIG. 6, there was a direct relationship between iron concentration and change in acetic acid space time yield. When iron concentration increased from approximately 450 to approximately 1750 wppm, the acetic acid space time yield decreased by greater than 10%, demonstrating a poisoning effect of iron on the rhodium catalyst system.

Example 3

Figure 7:
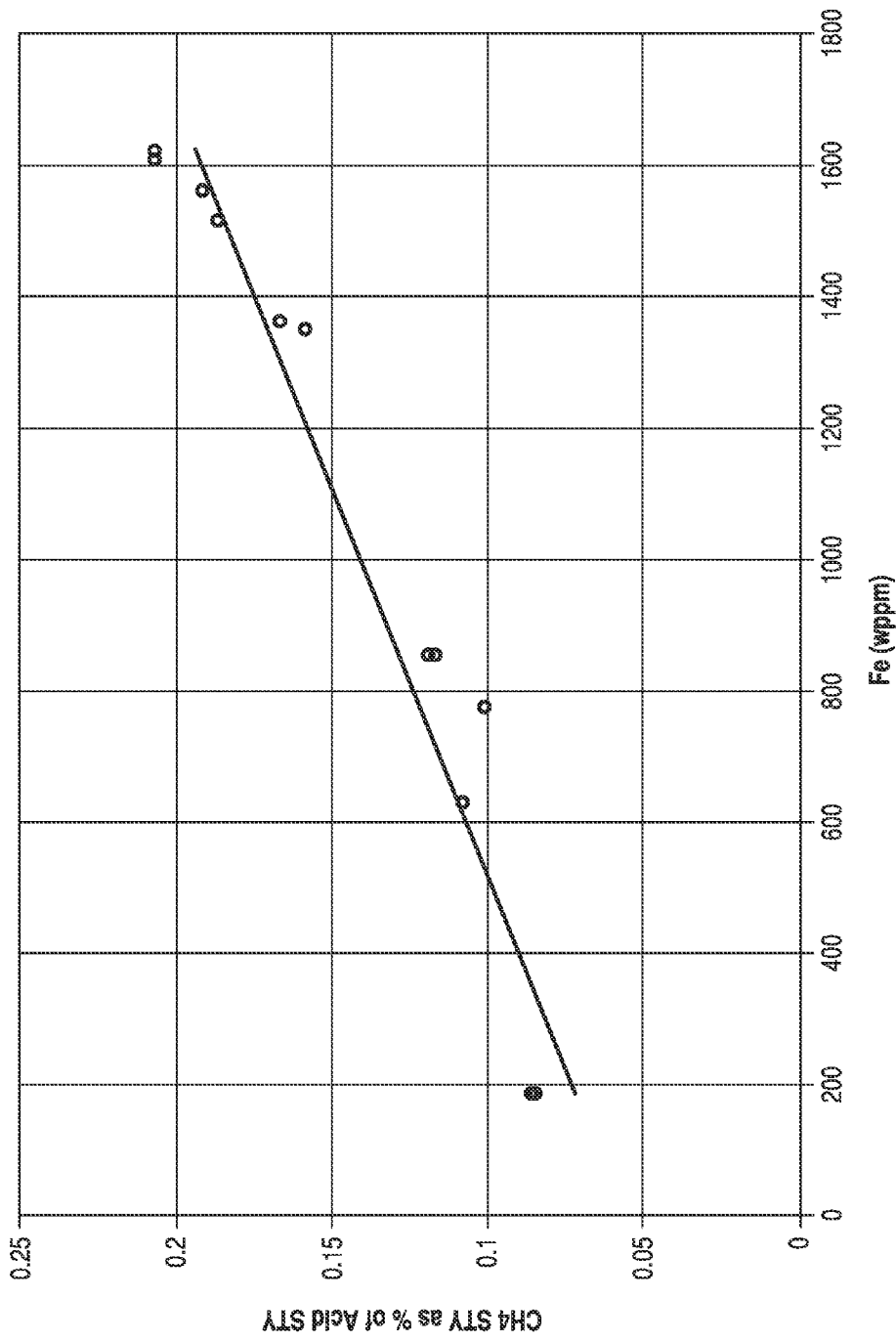
FIG. 7 illustrates the change in space time yield for methanol as a percentage of acetic acid space time yield versus iron concentration.

A portion of a reaction medium formed according to the process described herein as Example 2 was measured off-line at four discrete iron concentrations. As shown in FIG. 7, there was a direct relationship between iron concentration and change in methane space time yield as a percent of acetic acid space time yield.

We claim:

1. A process for producing acetic acid comprising:
   carbonylating at least one member selected from the group consisting of methanol, dimethyl ether, and methyl acetate in a reaction medium comprising water, a rhodium catalyst, methyl iodide and a halide salt, wherein the reaction medium comprises water in an amount from 0.1 to 14 wt. %;
   separating a portion of the reaction medium in a flash vessel to form a less volatile stream and a vapor product stream comprising acetic acid;
   recycling a liquid stream to the reactor, wherein the liquid stream comprises a portion of the less volatile stream;
   setting a threshold value of iron for the portion of the reaction medium, wherein the threshold value of iron concentration is a value selected within the range from 500 wppm to 1200 wppm;
   determining the iron content in the portion of the reaction medium; and
   removing at least a portion of the iron from the liquid stream when the iron content exceeds a threshold value.

2. The process of claim 1, wherein the reaction medium comprises acetaldehyde in an amount of no more than 1500 wppm.

3. The process of claim 1, wherein the less volatile stream comprises acetic acid in an amount from 60 to 90 wt. %, rhodium catalyst in an amount from 0.01 to 0.5 wt. % as rhodium, corrosion metals in a total amount from 10 to 2500 wppm, lithium iodide in an amount from 5 to 20 wt. %, methyl iodide in an amount from 1 to 25 wt. %, methyl acetate in an amount from 0.1 to 5 wt. %, and water in an amount from 0.1 to 8 wt. %.

4. The process of claim 1, further comprising separating the vapor product stream comprising acetic acid in a primary purification train to obtain an acetic acid product and one or more recycle streams.

5. The process of claim 4, wherein the liquid stream comprises a portion of the one or more recycle streams.

6. The process of claim 4, further comprising determining an iron content in the portion of the one or more recycle streams, and removing at least a portion of the iron from the portion of the one or more recycle streams when the iron content exceeds the threshold value.

7. The process of claim 1, wherein at least 5% of the iron is removed from the liquid stream.

8. The process of claim 1, wherein the rhodium catalyst is present in the reaction medium in an amount from 200 to 3000 wppm as rhodium.

9. The process of claim 8, wherein the iron concentration in wppm is maintained to be less than the concentration of the rhodium catalyst in wppm.

10. The process of claim 1, wherein the effective Space Time Yield of the rhodium catalyst is maintained above at least 80% of the maximum Space Time Yield.

11. The process of claim 1, wherein the effective Space Time Yield of the rhodium catalyst is maintained above at least 80% of the maximum Space Time Yield.

12. The process of claim 1, further comprising separating the vapor product stream comprising acetic acid in a primary purification train to obtain an acetic acid product and one or more recycle streams.

13. The process of claim 12, wherein the liquid stream comprises a portion of the one or more recycle streams.

* * * * *